US010786258B2

(12) United States Patent
Broyles et al.

(10) Patent No.: US 10,786,258 B2
(45) Date of Patent: Sep. 29, 2020

(54) MULTIPLE INFLATION ENDOVASCULAR MEDICAL DEVICE

(71) Applicant: W. L. Gore & Associates, Inc., Newark, DE (US)

(72) Inventors: Michael Broyles, Bellemont, AZ (US); Bret J Kilgrow, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 482 days.

(21) Appl. No.: 15/711,265

(22) Filed: Sep. 21, 2017

(65) Prior Publication Data

US 2019/0083103 A1    Mar. 21, 2019

(51) Int. Cl.
*A61B 17/12* (2006.01)
*A61M 25/10* (2013.01)
(Continued)

(52) U.S. Cl.
CPC .. *A61B 17/12131* (2013.01); *A61B 17/12109* (2013.01); *A61F 2/95* (2013.01);
(Continued)

(58) Field of Classification Search
CPC ... A61B 17/00; A61B 17/12; A61B 17/12022; A61B 17/12099; A61B 17/12136; A61B 17/12027; A61B 17/12109; A61B 17/12131; A61F 2250/0067; A61F 2/95; A61L 29/16; A61M 2025/0057;
(Continued)

(56) References Cited

U.S. PATENT DOCUMENTS

| 3,962,153 A | 6/1976 | Gore |
| 5,102,402 A | 4/1992 | Dror et al. |

(Continued)

FOREIGN PATENT DOCUMENTS

| EP | 0732087 A1 | 9/1996 |
| WO | WO-2012142540 A1 | 10/2012 |

(Continued)

OTHER PUBLICATIONS

International Search Report and Written Opinion received for PCT Patent Application No. PCT/US2018/035489, dated Sep. 27, 2018, 12 pages.

(Continued)

*Primary Examiner* — Jason E Flick

(57) ABSTRACT

A medical device may include a catheter, an expandable member, a cover, and an actuator. The catheter may include a longitudinal axis, proximal and distal ends, and a cover lumen extending from the proximal to the distal end. The expandable member may include proximal and distal ends and may be disposed on a distal section of the catheter. The cover may include a first region that may be disposed along the expandable member, and a second region that may extend along a length of the catheter beyond the proximal end of the expandable member towards the proximal end of the catheter. A first end of the cover may invert into the cover lumen. The actuator may be coupled to the first end of the cover and configured to move the first end of the cover towards the proximal end of the catheter along the longitudinal axis of the catheter.

16 Claims, 19 Drawing Sheets

(51) Int. Cl.
*A61M 25/00* (2006.01)
*A61F 2/95* (2013.01)
*A61L 29/16* (2006.01)

(52) U.S. Cl.
CPC ........ *A61M 25/0045* (2013.01); *A61M 25/10* (2013.01); *A61B 17/12027* (2013.01); *A61F 2250/0067* (2013.01); *A61L 29/16* (2013.01); *A61M 2025/0057* (2013.01); *A61M 2025/105* (2013.01); *A61M 2025/1081* (2013.01)

(58) Field of Classification Search
CPC .... A61M 2025/105; A61M 2025/1081; A61M 25/0045; A61M 25/10; A61M 25/00; A61M 25/0043; A61M 2025/1043
See application file for complete search history.

(56) References Cited

U.S. PATENT DOCUMENTS

| | | | |
|---|---|---|---|
| 5,246,421 A | 9/1993 | Saab | |
| 5,308,664 A | 5/1994 | House et al. | |
| 5,476,589 A | 12/1995 | Bacino | |
| 5,708,044 A | 1/1998 | Branca | |
| 6,039,721 A * | 3/2000 | Johnson | A61F 2/958 604/103 |
| 6,541,589 B1 | 4/2003 | Baillie | |
| 6,743,388 B2 | 6/2004 | Sridharan et al. | |
| 7,531,611 B2 | 5/2009 | Sabol et al. | |
| 8,637,144 B2 | 1/2014 | Ford | |
| 8,937,105 B2 | 1/2015 | Xu et al. | |
| 9,381,326 B2 | 7/2016 | Cully | |
| 9,415,193 B2 | 8/2016 | Campbell et al. | |
| 2005/0182361 A1 | 8/2005 | Lennox | |
| 2007/0156225 A1 | 7/2007 | George | |
| 2009/0182413 A1 | 7/2009 | Burkart et al. | |
| 2013/0253426 A1* | 9/2013 | Campbell | A61L 29/085 604/103.02 |
| 2016/0143579 A1 | 5/2016 | Martikka et al. | |
| 2019/0083101 A1 | 3/2019 | Broyles et al. | |

FOREIGN PATENT DOCUMENTS

| | | |
|---|---|---|
| WO | WO-2013172864 A3 | 11/2013 |
| WO | WO-2015017118 A3 | 2/2015 |

OTHER PUBLICATIONS

International Search Report and Written Opinion from PCT/US2018/035489, dated Sep. 27, 2018, 15 pages.
International Search Report and Written Opinion from PCT/US2018/035496, dated Sep. 18, 2018, 15 pages.

* cited by examiner

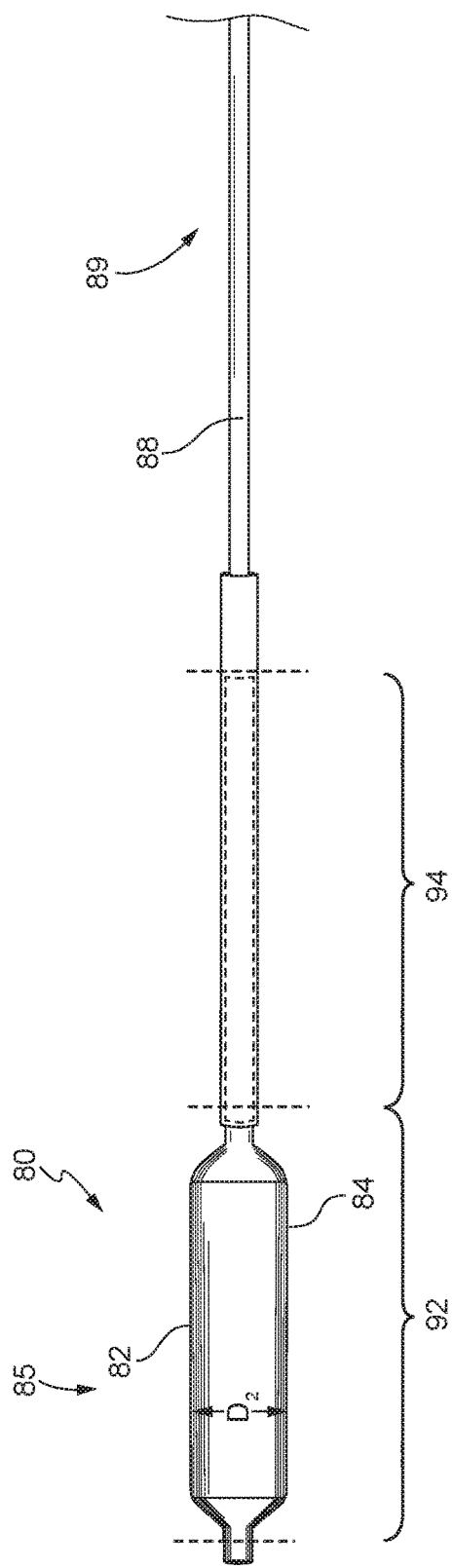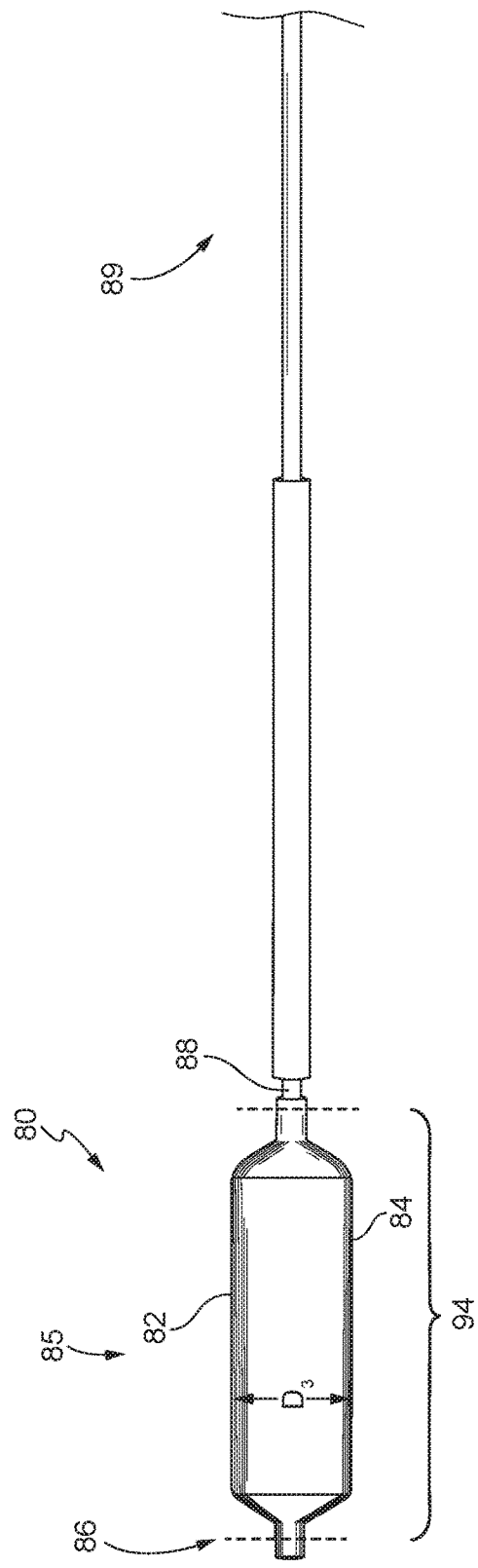

MULTIPLE INFLATION ENDOVASCULAR MEDICAL DEVICE

FIELD OF THE DISCLOSURE

This disclosure relates generally to occlusion and therapeutic agent delivery devices, systems, and methods, and in particular to occlusion and therapeutic agent delivery devices, systems, and methods configured for repeated inflations of a single expandable member having a longitudinally movable cover to provide multiple treatments or functional surfaces.

BACKGROUND

Vascular diseases, such as arthrosclerosis, artery occlusion, vascular prophylactic intervention, phlebitis, intimal hyperplasia, plaques, vascular dissections, peripheral artery disease, aneurismal disease, stenosis, and restenosis, are a leading cause of human mortality and morbidity. Vascular diseases arise from a variety of causes, and in some cases, necessitate surgical or endovascular intervention. Trauma to the vascular system can also necessitate surgical intervention to treat the traumatized anatomy. A common treatment for vascular disease is the short-term or long-term contact of a tissue with an endovascular medical device, such as a balloon or a stent, that is coated with a therapeutic agent that prevents or reduces vascular disease at the site of contact. Upon contact of the endovascular medical device with diseased vascular tissue, the therapeutic agent elutes from the endovascular medical device into the surrounding tissue at the site of contact, thereby treating the vascular disease at a local level. The long-term contact, e.g., implantation, of endovascular medical devices including vascular grafts, stent-grafts, and stents, and the short-term contact of vascular medical devices including catheter-based balloons, are often undertaken to treat vascular disease and vascular trauma.

The treatment of vascular disease at a local level, rather than a systemic level, is often preferred. Systemic administration of therapeutic agents (e.g., drugs and densified materials) can produce unwanted side effects when compared to the local administration of a therapeutic agent to treat vascular disease. Conventionally, the utilization of drug-coated endovascular medical devices has become a standard technique for the local administration of a drug to a target tissue. For example, drug-coated balloons (DCBs) have been used for the local administration of a drug to a target tissue to treat vascular disease, including coronary artery disease and peripheral artery disease (see, e.g., U.S. Pat. No. 5,102,402, issued to Dror et al. (hereafter "Dror")). Dror discloses placing a DCB in a blood vessel lumen to treat the vessel wall, inflating the DCB, and contacting an exterior surface of the DCB with the luminal vessel wall to deliver the drug into the blood vessel wall.

As described in Dror, many drug-coated endovascular medical devices, however, are configured for a single treatment or therapy via a single inflation of an expandable member having a single uniform functional surface. Conventional devices require an invasive surgical procedure to thread the drug-coated endovascular medical device to a therapeutic site and are suitable for only a single treatment at the site. After the single treatment, the expandable member is typically deflated and the drug-coated endovascular medical device is withdrawn from the body. In some circumstances, however, multiple treatments or multiple treatment surfaces at a therapeutic site may be desired. Accordingly, the need exists for occlusion and therapeutic agent delivery devices, systems, and methods capable of providing repeated treatments at a therapeutic site.

BRIEF SUMMARY

Various embodiments relate to a medical device including (i) a catheter including a longitudinal axis, a proximal end, a distal end, and a cover lumen extending from the proximal end of the catheter to the distal end of the catheter, and (ii) an expandable member including a proximal end and a distal end. The expandable member is disposed on a distal section of the catheter. The medical device further includes (iii) a cover including a first region and a second region. The first region is disposed along, e.g., overlaps or covers, the expandable member, and the second region extends along a length of the catheter beyond the proximal end of the expandable member toward the proximal end of the catheter. A first end of the cover inverts into the cover lumen adjacent the distal end of the catheter. The medical device further includes (iv) an actuator coupled to the first end of the cover and configured to retract the first end of the cover through the cover lumen towards the proximal end of the catheter along the longitudinal axis of the catheter.

In some embodiments, a medical device includes a catheter having a longitudinal axis, a proximal end, a distal end, and a cover lumen extending from the proximal end of the catheter to the distal end of the catheter. The medical device further includes an expandable member including a proximal end and a distal end. The expandable member may be disposed on the catheter. The medical device may further include a cover including a first region, a second region, and a third region. A first end of the cover may invert into the cover lumen. An actuator may be coupled to the first end of the cover and may be configured to move the first end of the cover towards the proximal end of the catheter along the longitudinal axis of the catheter. The first region may include a therapeutic agent disposed on a surface of the first region of the cover. The second region may include at least one aperture through which the expandable member may expand. The third region may include an endoprosthesis.

In certain embodiments, the cover includes polytetrafluoroethylene, expanded polytetrafluoroethylene, or expanded copolymers of polytetrafluoroethylene.

In various embodiments, the cover may have a length that is at least two times a working length of the expandable member. In some embodiments, a sheath is disposed along at least a portion of the second region of the cover. In some embodiments, the second region of the cover is less distensible than the expandable member. In certain embodiments, the therapeutic agent includes paclitaxel, docetaxel, protaxel, arsenic trioxide, thalidomide, atorvastatin, cerivastatin, fluvastatin, betamethasone diproprionate, dexamethasone21-palmitate, sirolimus, everolimus, zotarolimus, biolimus or temsirolimus.

In various embodiments, a medical device includes a catheter, an expandable member, a cover, and an actuator. The catheter may include a proximal end, a distal end, a cover lumen that extends from the distal end to the proximal end of the catheter. The expandable member may be disposed on the catheter and has a working length. The cover may include a plurality of regions and a first end of the cover may be inverted into a cover lumen of the catheter. The cover may have a length that is at least two times the working length of the expandable member. The actuator may be coupled to the first end of the cover and configured to move the first end of the cover towards the proximal end of the catheter along the longitudinal axis of the catheter.

In some embodiments, a therapeutic agent is disposed on a first region of the plurality of regions of the cover or a second region of a plurality of regions.

In some embodiments, a second therapeutic agent may be disposed on a surface of the other of the first region and the second region of the cover. In still yet other embodiments, a first endoprosthesis may be disposed on a surface of the other of the first region and the second region of the cover, still yet a second endoprosthesis may be disposed on a surface of a third region of the plurality of regions of the cover. In some embodiments, the first endoprosthesis may have a first length and the second endoprosthesis has a second length that may be different from the first length.

In certain embodiments, the first therapeutic agent may be different than the second therapeutic agent. In some embodiments, at least one of the first therapeutic agent and the second therapeutic agent comprises a densified material configured to increase a coefficient of friction on the surface of the region it is disposed on. In certain embodiments, the other of the first therapeutic agent and the second therapeutic agent that does not comprise a densisified material may comprise at least one of paclitaxel, docetaxel, protaxel, arsenic trioxide, thalidomide, atorvastatin, cerivastatin, fluvastatin, betamethasone diproprionate, dexamethasone21-palmitate, sirolimus, everolimus, zotarolimus, biolimus or temsirolimus.

In some embodiments, the first therapeutic agent and the second therapeutic agent are the same therapeutic agent. In certain embodiments the first therapeutic agent may be at a first dose density and the second therapeutic may be at a second dose density that is different from the first dose density.

In various embodiments, a third therapeutic agent is disposed on a surface of a third region of the plurality of regions of the cover, the third therapeutic agent may be different from at least one of the first and second therapeutic agents. In some embodiments, the first region of the plurality of regions has a length that is greater than a working length of the expandable member, and the second region of the plurality of regions may have a length that is also greater than the working length of the expandable member.

In some embodiments, a third region of the plurality of regions may include an endoprosthesis.

In various embodiments, a medical device includes a catheter, an expandable member, a cover, and an actuator. The catheter may include a longitudinal axis, a proximal end, a distal end, and a cover lumen extending from the proximal end of the catheter to the distal end of the catheter. The expandable member may include a proximal end and a distal end and may be disposed on the catheter. The cover may include a plurality of regions, and a first region of the plurality of regions may have at least one aperture. A first end of the cover may evert into the cover lumen. The actuator may be coupled to the first end of the cover and configured to move the first end of the cover towards the proximal end of the catheter along the longitudinal axis of the catheter.

In some embodiments, a second region of the plurality of regions comprises a therapeutic agent disposed on a surface of the second region.

In some embodiments, the first region of the plurality of regions is less distensible than the expandable member.

In some embodiments, the at least two regions of the plurality of regions each have a length that is at least as long as a working length of the expandable member.

In some embodiments, the at least one aperture comprises a portion of the first region that is weaker than the remaining portion of the first region of the plurality of regions.

In some embodiments, a second region of the plurality of regions further comprises an endoprosthesis.

In various embodiments a medical device includes a catheter, an expandable member, a cover, and an actuator. The catheter may include a longitudinal axis, a proximal end, a distal end, and a cover lumen extending from the proximal end of the catheter to the distal end of the catheter. The expandable member may include a proximal end and a distal end, and a working length. The expandable member may be disposed on the catheter. The cover may include a plurality of regions The actuator may be coupled to a first end of the cover configured to move the first end of the cover towards the proximal end of the catheter along the longitudinal axis of the catheter.

In some embodiments, a first region of the plurality of regions and a second region of the plurality of regions each have a length that is at least equal to the working length of the expandable member.

In some embodiments, a sheath may be disposed along at least a portion of a first region of the cover, wherein the first region of the cover extends between the proximal end of the expandable member and the proximal end of the catheter. Optionally, the cover may include at least one line that is coupled to the actuator. Optionally, the at least one line may be integral with the cover.

In some embodiments, a third region of the plurality of regions may have a length that is at least equal to the working length of the expandable member.

In some embodiments, a first region of the plurality of regions has a first nominal diameter, and a second region of the plurality of regions has a second nominal diameter that is different from the first nominal diameter. A third region of the plurality of regions may have a third nominal diameter that may be different from the first and second nominal diameters.

In some embodiments, a first region of the plurality of regions is positioned around the expandable member and a second region of the plurality of regions is positioned around the catheter.

In various embodiments, a method of treatment includes providing a medical device having an expandable member and a cover. The cover may include a first region and a second region. The method may include inserting the medical device in a peripheral blood vessel and expanding the expandable member with the first region of the cover positioned over the expandable member such that the first region of the cover provides a first treatment to a blood vessel wall. The actuator may be activated to draw the first region into a lumen of the medical device and to position the second region of the cover over the expandable member. The expandable member can be expanded with the second region of the cover over the expandable member such that the second region of the cover provides a second treatment to the blood vessel wall. The first treatment may be different from the second treatment, and each of the first treatment and the second treatment may be provided to the blood vessel wall prior to removing the medical device assembly from the body lumen.

In some embodiments, the at least one of the first treatment and the second treatment may include transferring a therapeutic agent to the blood vessel wall.

In some embodiments, the second region of the cover includes a plurality of apertures through which an expandable member expands. Providing the second treatment may include contacting and shaving deposits from a surface of blood vessel wall. Optionally, the method may also include expanding the expandable member with a third region of the cover over the expandable member such that the third region of the cover provides a third treatment to the blood vessel wall. Each of the first treatment, the second treatment, and the third treatment may be provided to the blood vessel wall prior to removing the medical device assembly from the blood vessel.

In some embodiments, the third treatment may include positioning an endoprosthesis positioned around the third region of the cover into contact with at least a portion of the blood vessel wall.

In some embodiments, the first treatment may include transferring a first therapeutic agent to the blood vessel wall, and the second treatment may include transferring a second therapeutic agent to the blood vessel wall, the first therapeutic agent being different from the second therapeutic agent.

In some embodiments, the method of treatment may include expanding the expandable member with a third region of the cover over the expandable member such that the third region of the cover provides a third treatment to the blood vessel wall. The third region of the cover may include an endoprosthesis and the third treatment may include deploying the endoprosthesis in the blood vessel wall. In addition, each of the first treatment, the second treatment, and the third treatment may be provided to the blood vessel wall prior to removing the medical device assembly from the body lumen.

In some embodiments the first treatment may be performed prior to the third treatment, and the first treatment may include contacting and shaving deposits from a surface of blood vessel wall.

In some embodiments, the first treatment may include transferring a first therapeutic agent to the blood vessel wall.

In some embodiments, the first treatment is performed prior to the third treatment, and the second treatment may be performed after the third treatment. Optionally, the second region may include an endoprosthesis and the second treatment may include deploying a second endoprosthesis in the blood vessel well. Further, optionally a first diameter the endoprosthesis of the third region is different from a second diameter of the second endoprosthesis of the second region. Also optionally, a first length of the endoprosthesis of the third region may be different from a second length of the second endoprosthesis of the second region.

In some embodiments, the second treatment may include transferring a therapeutic agent to the blood vessel wall.

In some embodiments, the method includes expanding the expandable member with a fourth region of the cover over the expandable member such that the fourth region of the cover provides a fourth treatment to the blood vessel wall. The first treatment, the second treatment, the third treatment, and the fourth treatment may be provided to the blood vessel wall prior to removing the medical device assembly from the body lumen.

In accordance with some aspects, the cover is formed, at least in part, of an expanded fluoropolymer. Optionally, the expanded fluoropolymer includes expanded polytetrafluoroethylene, expanded polytetrafluoroethylene, or an expanded copolymer of polytetrafluoroethylene.

BRIEF DESCRIPTION OF THE DRAWINGS

The accompanying drawings are included to provide a further understanding of the embodiments of the disclosure provided herein and are incorporated in and constitute a part of this specification, illustrate embodiments of the disclosure and together with the description serve to explain the principles of the embodiments of the disclosure.

FIG. 6B is a side view of the expandable member assembly including a second region of the cover disposed along the expandable member in an inflated state at a second nominal diameter, in accordance with an embodiment of the disclosure;

FIG. 6C is a side view of the expandable member assembly including a third region of the cover disposed along the expandable member in an inflated state at a third nominal diameter, in accordance with an embodiment of the disclosure;

DETAILED DESCRIPTION

I. Introduction

Figure 1:
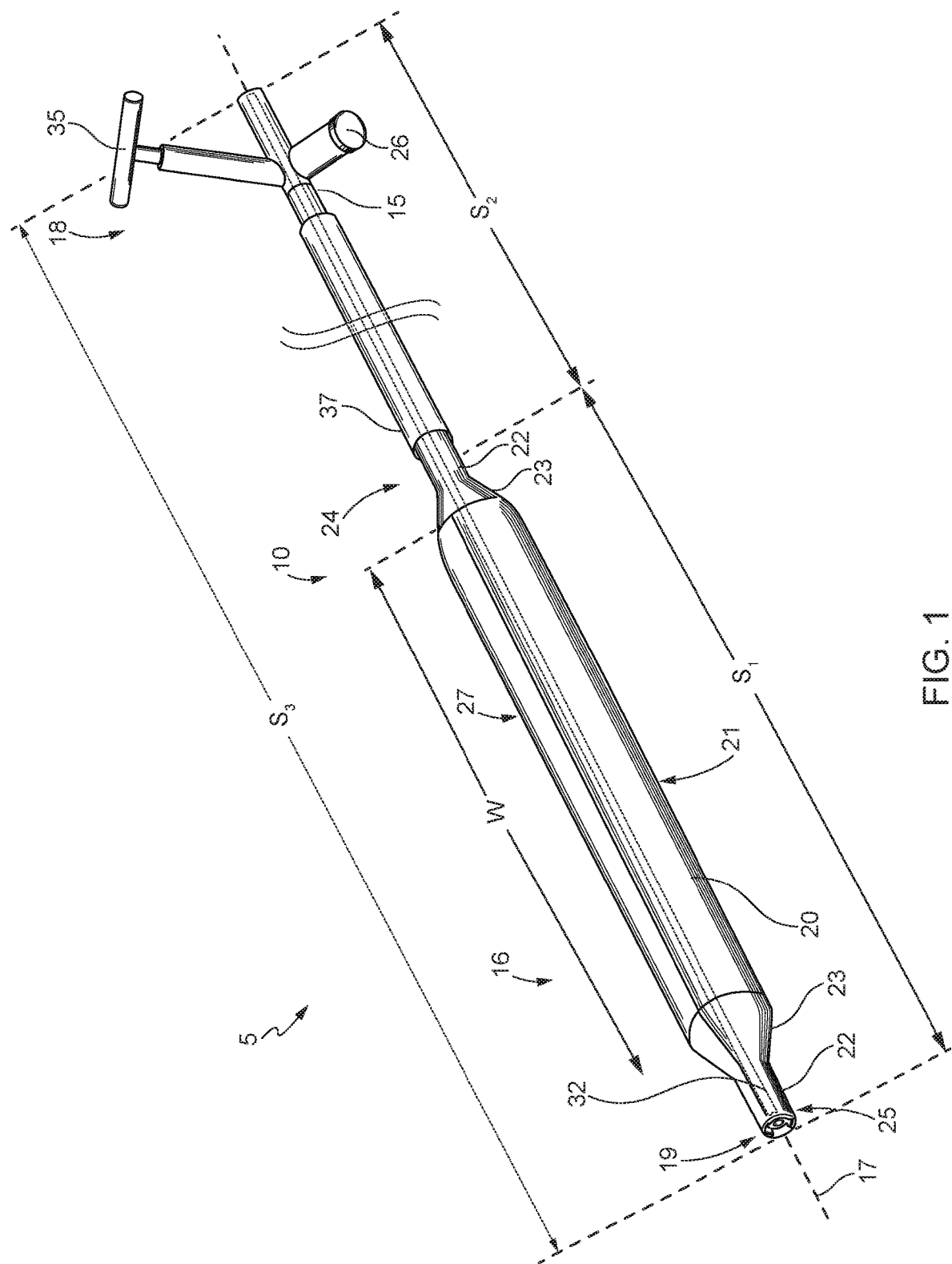
FIG. 1 is perspective view of a medical device including an expandable member assembly and a catheter, in accordance with an embodiment of the disclosure.

Various embodiments described herein are directed to occlusion and therapeutic agent delivery devices, systems, and methods capable of deploying an expandable member within a lumen of a tubular structure (e.g., a blood vessel or duct) to treat a site on the tubular structure, and inflating the expandable member to a nominal diameter such that a surface of the expandable member (or a cover on the expandable member) contacts a wall of the tubular structure to deliver the treatment or therapy to the site on the tubular structure. A problem associated with many conventional occlusion and therapeutic agent delivery devices, systems, and methods is that the expandable member (or the cover on the expandable member) is only configured with a single treatment surface or therapy. After the single treatment surface or therapy is administered, the expandable member is typically deflated and the device is withdrawn from the body.

Various embodiments described herein are directed to occlusion and therapeutic agent delivery devices, systems, and methods capable of repeated inflations of a single expandable member having a longitudinally movable cover to provide multiple treatments or functional surfaces. For example, various embodiments of the present disclosure are directed to a medical device that includes (i) a catheter including a longitudinal axis, a proximal end, a distal end, and a cover lumen extending from the proximal end of the catheter to the distal end of the catheter, and (ii) an expandable member including a proximal end and a distal end. The expandable member is disposed on a distal section of the catheter. The medical device further includes (iii) a cover including a first region and a second region. The first region is disposed along, e.g., overlaps or covers, the expandable member, the second region extends along a length of the catheter beyond the proximal end of the expandable member towards the proximal end of the catheter, and a first end of the cover inverts into the cover lumen. The medical device further includes (iv) an actuator coupled to the first end of the cover and configured to retract the first end of the cover through the cover lumen towards the proximal end of the catheter along the longitudinal axis of the catheter. As a portion of the cover is retracted into the cover lumen, an unretracted outer portion of the cover is pulled in the distal direction toward the distal end of the catheter, such that a previously undeployed region of the cover is positioned over the expandable member for subsequent treatment or therapy at the therapeutic site.

Advantageously, this approach provides occlusion and therapeutic agent delivery devices, systems, and methods that are capable of repeated inflations of a single expandable member having a longitudinally movable cover to provide multiple treatments or functional surfaces at a treatment site. For example, the movable cover may be segmented into a plurality of regions, each region having a specific therapeutic agent coating (e.g., same or different drug and/or dose of drug), inflation profile (e.g., same or different nominal diameter), functional surface (e.g., same or different surface texture and/or surface features), and or endoprosthesis device (e.g., an expandable stent, a self-expanding stent, one or more stents having the same or different diameters and/or lengths). Moreover, the therapeutic agent delivery devices, systems, and methods optionally include a cylindrical sheath disposed along at least a portion of the movable cover that overlaps and protects one or more regions of the movable cover during deployment to the therapeutic site. The sheath may further protect one or more regions of the movable cover while the expandable member expands and radially presses an exposed region covering the expandable member against a therapeutic site.

II. Definitions

As used herein, the terms "a" and "an" are defined as one or more unless this disclosure explicitly requires otherwise.

The preposition "between," when used to define a range of values (e.g., between x and y) means that the range includes the end points (e.g., x and y) of the given range and the values between the end points.

As used herein, the term "coating" refers to one or more materials disposed on the surface of a substrate. In the present disclosure the substrate may include the structural layer or substrate or expandable member or cover. The coating may lie completely on the surface or may be incorporated, in whole or in part, within the openings or pores present in a substrate. The latter coating configuration is commonly referred to in the art as "imbibed" or "filled" materials.

As used herein, the terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, any of the present devices, systems, and methods that "comprises," "has," "includes" or "contains" one or more elements possesses those one or more elements, but is not limited to possessing only those one or more elements. Likewise, an element of a device, system, or method that "comprises," "has," "includes" or "contains" one or more features possesses those one or more features, but is not limited to possessing only those one or more features.

Any of the present devices, systems, and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

As used herein, "delivery diameter" refers to the diameter or cross-sectional width of a tubular form that is substantially equal to or slightly larger than the diameter or cross-sectional width of the tubular form during delivery through the vasculature, pre-inflation.

As used herein, "deployment" refers to the actuation or placement of a device at a treatment or therapeutic site. Deployment process can occurs in stages.

As used herein, the terms "first", "second", "third" . . . "sixth", etc. identify and distinguish particular regions or components of the occlusion and therapeutic agent delivery devices and are not used herein to indicate a specific order of deployment, unless otherwise stated.

As used herein, the term "invert" refers to a material doubling back on itself internally or externally.

As used herein, the terms "micropores" and "microporous" refer to openings in materials, for example the area between expanded polytetrafluoroethylene (ePTFE), nodes and fibrils. Usually, as in the case of ePTFE, these micropores contain air when the material is not "wetted".

As used herein, a "non-compliant" balloon is one that has less than about 10% diametric growth when inflated from the nominal inflation pressure to the rated burst pressure.

As used herein, "nominal diameter" means the approximate diameter of the balloon at the nominal inflation pressure. Beyond this state, pressure increases (e.g., up to the rated burst pressure) result in less than a 20% increase in diameter, less than a 15% increase in diameter, or less than a 10% increase in diameter. Typically, the nominal diameter is the labeled diameter as indicated on the instructions for the end user, e.g., a clinician.

As used herein, the terms "proximal" and "distal" are similarly used for the purpose of identifying and distinguishing particular regions or components of the occlusion and therapeutic agent delivery devices. "Proximal" is used to identify a location or portion of the assembly that when inserted is closer to a physician or clinician and/or is closer to an entry site through which the assembly is passed. "Distal" is used to identify a location or portion of the assembly that is farther from the physician or clinician and/or farther from the entry site through which the assembly is passed. The term "longitudinal" refers to the lengthwise direction relative to the device, and the term "lateral" refers to a direction perpendicular to the longitudinal direction, e.g., the width of a device.

As used herein, a "semi-compliant" balloon is one that has less than about 20% diametric growth (e.g., less than a 20% increase in the balloon diameter relative to the nominal diameter) when inflated from the nominal inflation pressure to the rated burst pressure.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. The term "majorly" indicates at least half.

As used herein, the term "variably permeable microstructure" refers to a structure or material with a resistance to fluid transfer at a first state that is greater than the resistance of the same structure or material at a second state with such resistance varying between the two states. One skilled in the art will appreciate various methods which characterize the change in permeability from testing at a first state and comparing to testing done at a second state. These methods include, but are not limited to, characterizations of air or liquid flux across the microstructure at a given pressure differential, characterization which determines the pressure differential at which different fluids strike through the microstructure such as Water Entry Pressure or Bubble Point, characterization of porosity, and visual characterization such as inter-nodal or inter-fibril spacing as measured from an image (e.g. from a scanning electron microscope or light microscope). One non-limiting embodiment of a variable permeable material comprises a material that has a substantially closed microstructure when the material is not under a strain and has a more open microstructure when the material is strained.

As used herein, the terms "wet", "wet-out" and "wetted" refer to the displacement of air in a microporous material by a fluid. Wetting of a material lowers the resistance to subsequent fluid transfer and facilitates the flow of fluids though the microporous material. Furthermore, these microporous materials are intended to be open cell structures, meaning the micropores are interconnected, and not closed cell structures. This allows fluid to flow through the material. Capillary effects may also play an important role in fluid flow though the material as wetting occurs, especially for highly porous materials with small interconnected pores. Wetting can be accomplished with the aid of one or more surfactants added to the fluid. The surfactant can absorb onto the fluid-vapor, solid-fluid, and solid-vapor interfaces, which in turn modifies the wetting behavior of hydrophobic materials. The wetting will also depend on the viscosity to the fluid As used herein, the term "working length" is the length of the substantially straight body section of an expandable member (e.g., a balloon), which corresponds to the approximate length of the expandable member between the opposed shoulder/tapered portions as shown by "W" in FIG. 1.

III. Occlusion and Therapeutic Agent Delivery Devices and Systems

FIG. 1 shows a medical device 5 that includes an expandable member assembly 10 and a catheter 15. In various embodiments, the catheter 15 has a cylindrical form and comprises a longitudinal axis 17, a proximal end 18, a distal end 19, and a cover lumen 32 optionally extending from the proximal end 18 to the distal end 19. The expandable member assembly 10 comprises an inflatable member or expandable member 20 positioned on a distal section 16 of the catheter 15. As shown, the expandable member 20 includes a body section 21 that may be substantially cylindrical along a working length (W), two opposed leg portions 22, and shoulder/tapered portions 23 that may be integrally connected to the body section 21 and the two opposed leg portions 22. The body section 21, the leg portions 22, and the shoulder/tapered portions 23 define an overall length of the expandable member 20 from a proximal end 24 to a distal end 25. In some embodiments, the expandable member 20 comprises a thermoplastic polymeric material that includes urethanes, PET, PEBAX, polytetrafluoroethylene (PTFE), polyamides such as nylon 12, nylon 11, nylon 9, nylon 6/9, nylon 6/6, and combinations thereof.

The medical device 5 has a first section $S_1$ that extends from a distal end 19 of the catheter 15 to the proximal end 24 of the expandable member 20. The medical device 5 also has a second section $S_2$ that extends from the proximal end 24 of the expandable member 20 to the proximal end 18 of the catheter 15. The medical device 5 also has a third section $S_3$ that corresponds to a length of the catheter 15 that extends from the distal end 19 of the catheter 15 to the proximal end 18 of the catheter 15 within the cover lumen 32 of the catheter 15.

The working length (W) of the expandable member 20 may be from about 10 mm to about 400 mm, from about 10 mm to about 250 mm, or from about 10 mm to 150 mm. Similarly, the nominal diameter of the expandable member 20 can be from about 2 mm to about 100 mm, from about 2 mm to about 60 mm, or from about 2 mm to about 30 mm. By way of example, the expandable member 20 can have a nominal diameter of from about 4 mm to about 10 mm and a working length (W) of from about 25 mm to about 50 mm, or a nominal diameter of from about 6 mm to about 25 mm and working length (W) of from about 15 mm to about 75 mm. As should be understood, the expandable member 20 may have any appropriate dimension and size for the clinical application.

In various embodiments, the expandable member 20 is attached or mounted to the catheter 15 at the leg portions 22 such that the catheter 15 is in fluid communication with the expandable member 20. For example, the catheter 15 may comprise one or more lumens, one of which may be in fluid communication, optionally through an orifice in the catheter, with a chamber of the expandable member 20 for supplying inflation fluid to inflate the expandable member 20 balloon in a tubular structure such as a patient's vasculature. The catheter 15 may be coupled, for example via a port 26, to any suitable inflation-deflation device, such as a syringe, an indeflator, pump or any other apparatus for conducting inflation fluid through the catheter 15 and into the expandable member 20. In accordance with some embodiments, the inflation-deflation device may push fluid into and retract fluid from the chamber of the expandable member 20 via the catheter 15 to inflate and deflate the expandable member 20. To assist in the control of the diameter of a balloon, the catheter 15 and the expandable member 20 may be aspirated (remove air and replace it with a fluid) prior to inflating the expandable member 20 with inflation fluid. The inflation fluid used to aspirate the catheter 15 and the expandable member 20 and/or to inflate the expandable member 20 may comprise a contrast (e.g., an imaging agent that allows the expandable member 20 to be imaged by an imaging modality), or a mixture of a contrast and saline.

The expandable member assembly 10 also further comprises a cover 27. The cover 27 includes a plurality of regions that may be disposed throughout the first section $S_1$, second section $S_2$, and third section $S_3$ of the medical device 5. In various embodiments, the cover 27 has a first region distributed along the first section $S_1$ of the medical device 5. In other embodiments, the cover 27 has a first region distributed along the first section $S_1$ of the medical device and a second region distributed along the second section $S_2$ of the medical device 5. In certain embodiments, the cover 27 has a first region distributed along the first section $S_1$ of the medical device 5, a second region distributed along a portion of the second section $S_2$ of the medical device 5, and—another region distributed along another portion of the second section $S_2$ of the medical device. The cover 27 also has a region that is inverted into the cover lumen 32 and is distributed along the third section $S_3$ of the medical device 5 within the cover lumen 32 of the catheter 15. In various embodiments, a total length of the regions of cover 27 distributed along the first section $S_1$ and second section $S_2$ of the medical device 5 is multiple times (e.g., 1×, 2×, 3×, 4×, or from 2 to 8 times, or from 2 to 4 times) longer than the overall length of the expandable member 20. In some embodiments, a total length of the regions of cover 27 distributed along the first section $S_1$ and second section $S_2$ of the medical device 5 is multiple times (e.g., 1×, 2×, 3×, 4×, or from 2 to 8 times, or from 2 to 4 times) longer than the working length (W) of the expandable member 20. The total length of the regions of the cover 27 distributed along the first section $S_1$ and second section $S_2$ of the medical device 5 may be from about 50 mm to about 2000 mm, from about 50 mm to about 1250 mm, or from about 50 mm to about 750 mm.

In some embodiments, during manufacture or assembly the cover, for example cover 27, is initially positioned within the cover lumen and then is inverted or folded back over the expandable member. In some embodiments, during manufacture or assembly the cover, for example cover 27, is initially positioned over the expandable member and then is inverted or folded into the cover lumen.

In some embodiments, the cover 27 comprises a porous layer, for example but not limited to a porous fluoropolymer layer. In accordance with certain embodiments, the porous fluoropolymer layer may include, without limitation, perfluoroelastomers and the like, polytetrafluoroethylene (PTFE) and the like, and expanded fluoropolymers and the like. Non-limiting examples of expandable fluoropolymers include ePTFE, expanded modified polytetrafluoroethylene, and expanded copolymers of polytetrafluoroethylene. For example, an extruded ePTFE tube, a helical wrapped ePTFE tube, or a cigarette wrapped ePTFE tube.

Various expandable blends of PTFE, expandable modified PTFE, and expanded copolymers of PTFE are disclosed in the art, such as in U.S. Pat. No. 5,708,044 to Branca; U.S. Pat. No. 6,541,589 to Baillie; U.S. Pat. No. 7,531,611 to Sabol et al.; U.S. Pat. No. 8,637,144 to Ford; and U.S. Pat. No. 8,937,105, to Xu et al. US Publication No. US20160143579 discloses additional embodiments as well as methods of making embodiments suitable for use herein.

In accordance with various embodiments, a plurality of regions of the cover 27 (e.g., first, second, and third regions) distributed along the first section $S_1$ and second section $S_2$ of the medical device 5 are configured to move longitudinally in the distal direction over the expandable member 20 throughout deployment of the expandable member assembly 10 within a tubular structure of a patient such that repeated inflations of the expandable member 20 may result in different regions of the cover 27 applying multiple treatments or functional surfaces to the tubular structure, without removal of the assembly 10 from a body lumen in which it is positioned. In some embodiments, the cover 27 wraps around the entire circumference of the expandable member 20 and covers the entire length of the expandable member 20 from the proximal end 24 to the distal end 25. In other embodiments, the cover 27 wraps around a portion of the circumference of the expandable member 20 and/or covers a portion of the length of the expandable member 20 from the proximal end 24 to the distal end 25.

In accordance with various embodiments, the medical device 5 may further include an actuator 35 coupled to a first end of the cover 27 that has been inverted into a cover lumen 32 (one of the one or more lumens in the catheter 15) of the catheter 15. The actuator 35 is configured via a mechanical system (e.g., a traditional deployment knob or a handle containing a mechanical advantage by use of a knob or a slider) to move the portions of the cover 27 throughout deployment of the expandable member assembly 10 such that repeated inflations of the expandable member 20 result in different portions of the cover 27 applying multiple treatments or functional surfaces. For example, a length of the cover 27 may be inverted into the cover lumen 32 at the distal end 19 of the catheter 15 be disposed along at least a portion of the third section $S_3$ of the medical device 5. The cover 27 positioned within the third section $S_3$ may be moved (e.g., pulled) via the actuator 35 through the cover lumen 32 towards the proximal end 18 of the catheter 15. Alternatively, in some embodiments a length of the cover 27 may be inverted into the cover lumen 32 at the proximal end 18 of the catheter 15 and moved (e.g., pulled) via the actuator 35 through the cover lumen 32 towards the distal end 19 of the catheter 15. Consequently, as the cover 27 is pulled through the cover lumen 32 a region of the cover 27 that was originally disposed along the catheter 15 towards the proximal end 18 is moved along the length of the catheter 15 towards the distal end 19 of the catheter 15 such that the region of the cover 27 becomes disposed along the expandable member 20.

In some embodiments where the cover 27 comprises a porous layer, one or more coatings may be applied to the porous layer. The one or more coatings may include therapeutic agents that may be applied to a region of the cover 27 such that a therapeutic agent coating substantially covers the working length (W) of the expandable member 20. Alternatively, the one or more therapeutic agent coatings may be applied to a portion of the cover 27 such that a therapeutic agent coating substantially covers the working length (W) of the expandable member 20 and is disposed on at least a region of the opposed leg regions 22 and/or shoulder/tapered regions 23. The same therapeutic agent coating may be disposed on one or more regions of the cover 27, one or more different therapeutic agent coatings may be disposed on one or more regions of the cover 27, no coating may be disposed on one or more regions of the cover 27, and/or a therapeutic agent coating may include one or more radiopaque elements, as described in further detail herein.

In some embodiments, the outer surface of the cover 27 and/or the expandable member 20 may have a surface texture and/or surface feature. The surface texture and/or surface feature may be part of a region of the cover 27 and/or the expandable member 20 such that the surface texture and/or surface feature extends along the working length (W) of the expandable member 20. Alternatively, the surface texture and/or surface feature may be part of a region of the cover 27 and/or the expandable member 20 such that the surface texture and/or surface feature extends along the working length (W) of the expandable member 20 and is disposed on at least a portion of the opposed leg portions 22 and/or shoulder/tapered portions 23. The same surface texture and/or surface feature may be disposed on one or more regions of the cover 27, one or more surface texture and/or surface feature may be disposed on one or more regions of the cover 27, no surface texture and/or surface feature may be disposed on one or more regions of the cover 27, and/or a surface texture and/or surface feature may include one or more radiopaque elements, as described in further detail herein.

In some embodiments, one or more endoprosthesis may be disposed on one or more regions of the cover 27. An endoprosthesis may be positioned on a region comprising an additional surface feature and/or a therapeutic agent coating. In other embodiments, an endoprosthesis may be positioned on a region of the cover 27 without any additional surface features or therapeutic agent coatings.

The expandable member assembly 10 may further comprise a cylindrical sheath 37 disposed along at least a portion of the second section $S_2$ of the medical device 5 about a portion of the cover 27. In some embodiments, the sheath 37 wraps around the entire circumference of the cover 27 and covers an entire length of the cover 27 disposed along the second section $S_2$ of the medical device 5. In other embodiments, the sheath 37 wraps around a portion of the circumference of the cover 27 and/or covers a portion of the cover 27 disposed along the second section $S_2$ of the medical device 5. The sheath 37 may protect a therapeutic agent coating (e.g., a drug coating or a densified coating) on an outer surface of the cover 27 positioned beneath the sheath 37 during placement of the expandable member assembly 10 in the tubular structure of a patient. The sheath 37 may also retain a portion of the cover 27 positioned beneath the sheath 37 at a delivery diameter during the use of the expandable member assembly 10. In some embodiments, the sheath 37 is bonded to a region of the catheter 15 by an adhesive. For example, the sheath 37 may be bonded to a handle or hub at the proximal end 18 of the catheter 15. In other embodiments, the sheath 37 is not bonded to the catheter 15. In various embodiments, the sheath 37 may comprise a polymer tube or a tube comprising other suitable materials, including but not limited to thermoplastics, for example but not limited to Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Polyamides such as nylon-11 and nylon-12, Polyoxymethylene (POM or Acetal), Polyethylene Terephthalate (PET, Thermoplastic Polyester), Polybutylene Terephthalate (PBT, Thermoplastic Polyester), Polyimide (PI, Imidized Plastic), Polyamide Imide (PAI, Imidized Plastic), Polybenzimidazole (PBI, Imidized Plastic); Polysulfone (PSU), Polyetherimide (PEI), Polyether Sulfone (PES), Polyaryl Sulfone (PAS); Polyphenylene Sulfide (PPS), Polyetheretherketone (PEEK); Fluoropolymers that include Fluorinated Ethylene Propylene (FEP), Ethylene Chlorotrifluoroethylene (ECTFE), Ethylene, Ethylene Tetrafluoroethylene (ETFE), Polychlortrifluoroethylene (PCTFE), Polyvinylidene Fluoride (PVDF), Perfluoroalkoxy (PFA), or combinations, copolymers, or derivatives thereof. Other commonly known medical grade materials include elastomeric organosilicon polymers, polyether block amide (e.g., PEBAX®). In particular, polyamides can include nylon 12, nylon 11, nylon 9, nylon 6/9, and nylon 6/6. In certain embodiments, PET, nylon, and PE may be selected for medical balloons used in coronary angioplasty or other high pressure applications. The specific choice of materials depends on the desired characteristics/intended application of the balloon.

Figure 2:
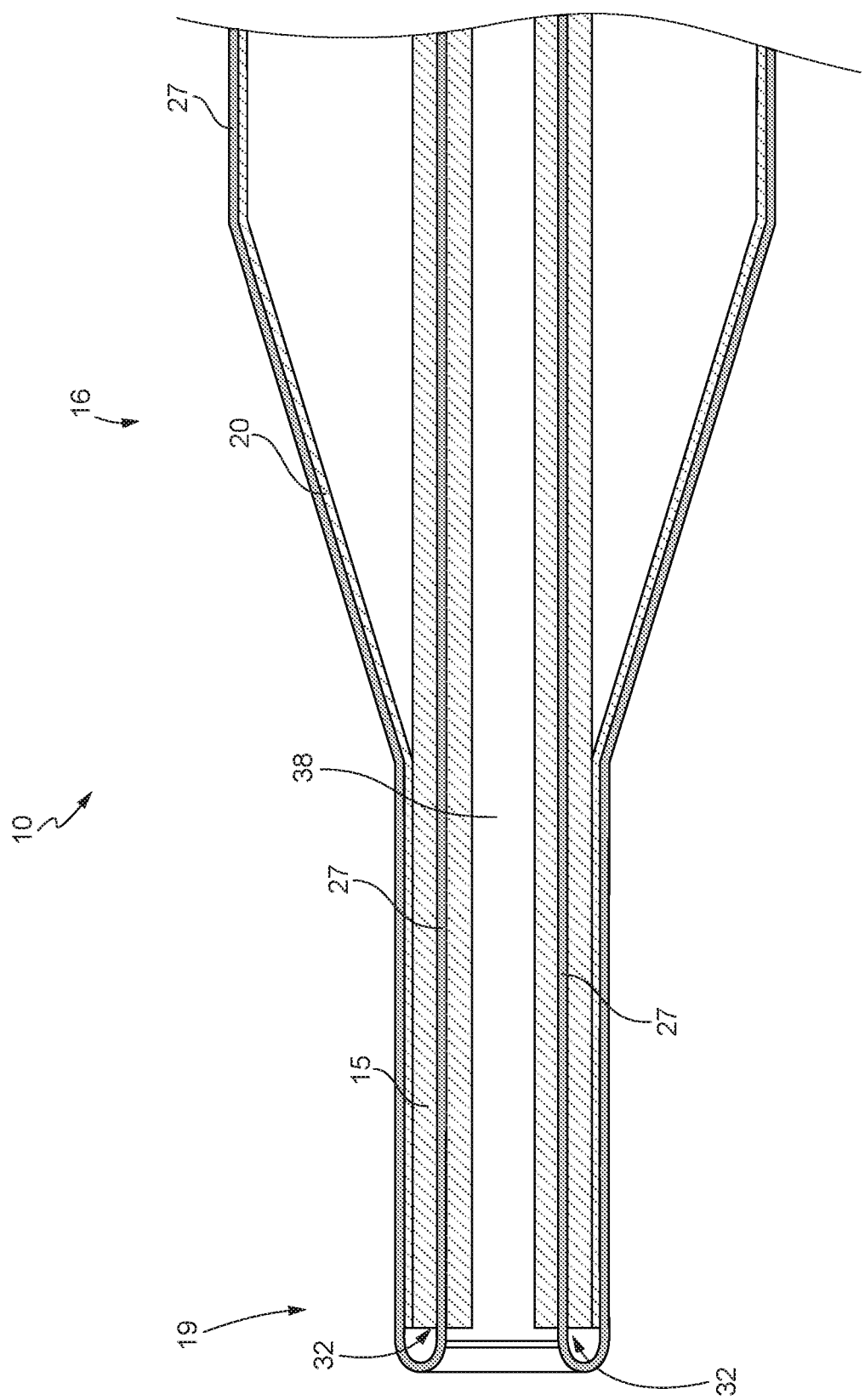
FIG. 2 is a side cross-sectional view of a distal region of the expandable member assembly, in accordance with an embodiment of the disclosure.

FIG. 2 depicts a cross-sectional view of a region of the medical device that includes a portion of the expandable member assembly 10 at the distal end 19 of the catheter 15. While FIG. 2 depicts the cover 27 positioned on an outer surface of the expandable member 20, in some embodiments additional elements may be positioned between the outer surface of the expandable member 20 and the cover 27, for example an endoprosthesis (e.g., a stent). In some embodiments, one or more endoprosthesis may be positioned on an outer surface of the cover 27. The cover 27 may invert into the distal end 19 of the catheter 15 and enter the cover lumen 32 of the catheter 15. In the embodiment shown in FIG. 2, the cover lumen 32 that receives the cover 27 comprises two openings. The cover 27 is split into two sections, each section entering a respective opening that together define the cover lumen 32. As the cover 27 is pulled through the cover lumen 32 the cover 27 may be further separated into two sections. The catheter 15 also include a guide wire lumen 38 and an inflation lumen 40 (not visibly distinct from the guide wire lumen 38 in the cross-sectional view of FIG. 2). In some embodiments, an optional tip may be secured by an adhesive or another suitable form of bonding to the distal end 19 of the catheter 15 at a tip of the catheter 15.

Figure 3:
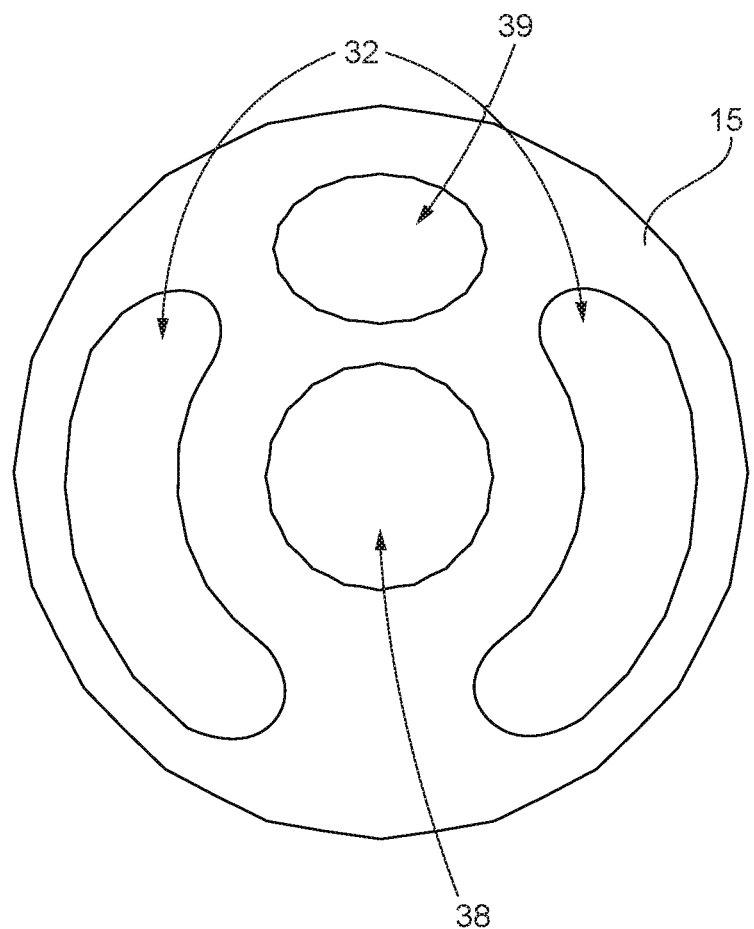
FIG. 3 is a front cross-sectional view of the catheter including a cover lumen, in accordance with an embodiment of the disclosure.

FIG. 3 depicts a front cross-sectional view of the catheter 15. The catheter 15 has openings that together define the cover lumen 32 that receives the cover 27. The catheter 15 also includes the guide wire lumen 38 that may receive a guide wire. The catheter 15 also includes the inflation lumen 39 that may be in fluid communication with the expandable member 20. As shown in FIG. 2, a portion of the cover 27 inverts into the cover lumen 32 and extends through the cover lumen 32 along the length of the catheter 15. The portion of the cover 27 that inverts into the cover lumen 32 is coupled at an end (not shown) to the actuator.

Figure 9:
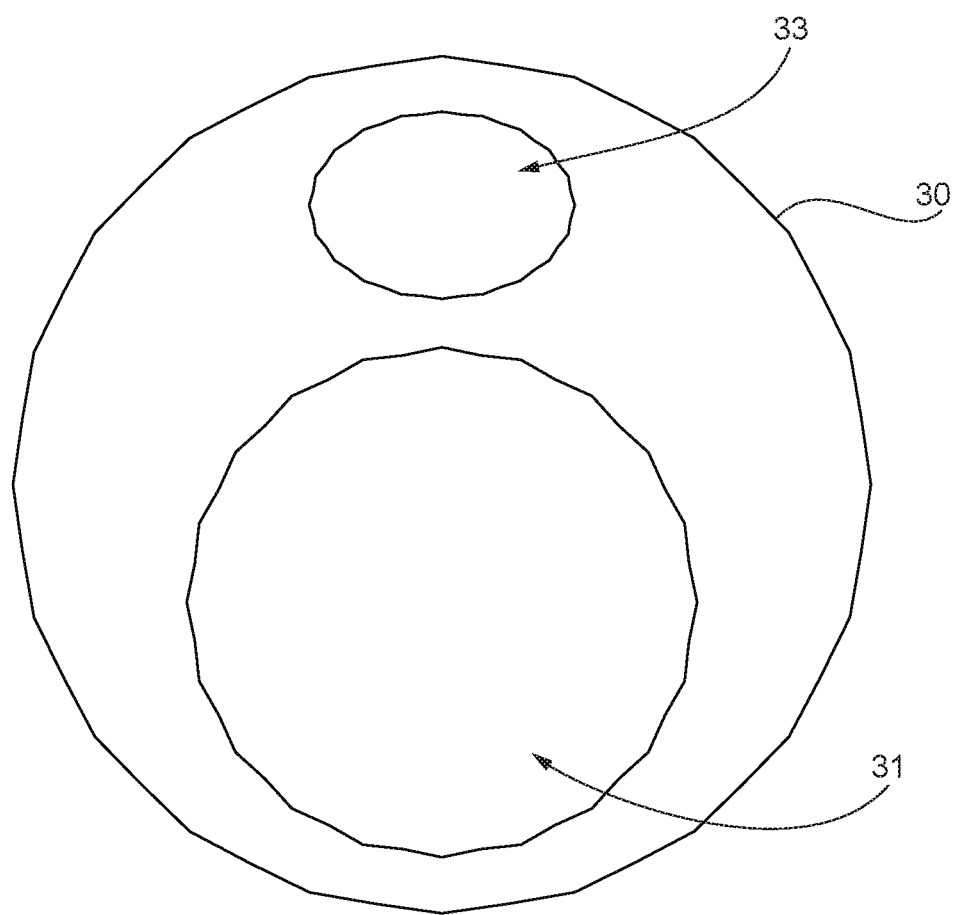
FIG. 9 is a front view of a catheter, in accordance with an embodiment of the disclosure.

In some embodiments, the cover lumen 32 comprises more or fewer openings that receive the cover 27. For example as shown in FIG. 9, in some embodiments a catheter 30 for use in a medical device of the present disclosure can include a cover lumen 31 comprising a single opening. The catheter 30 can also include an inflation lumen 33. In some embodiments, the catheter 30 may also include an additional lumen for a guide wire.

Figure 4:
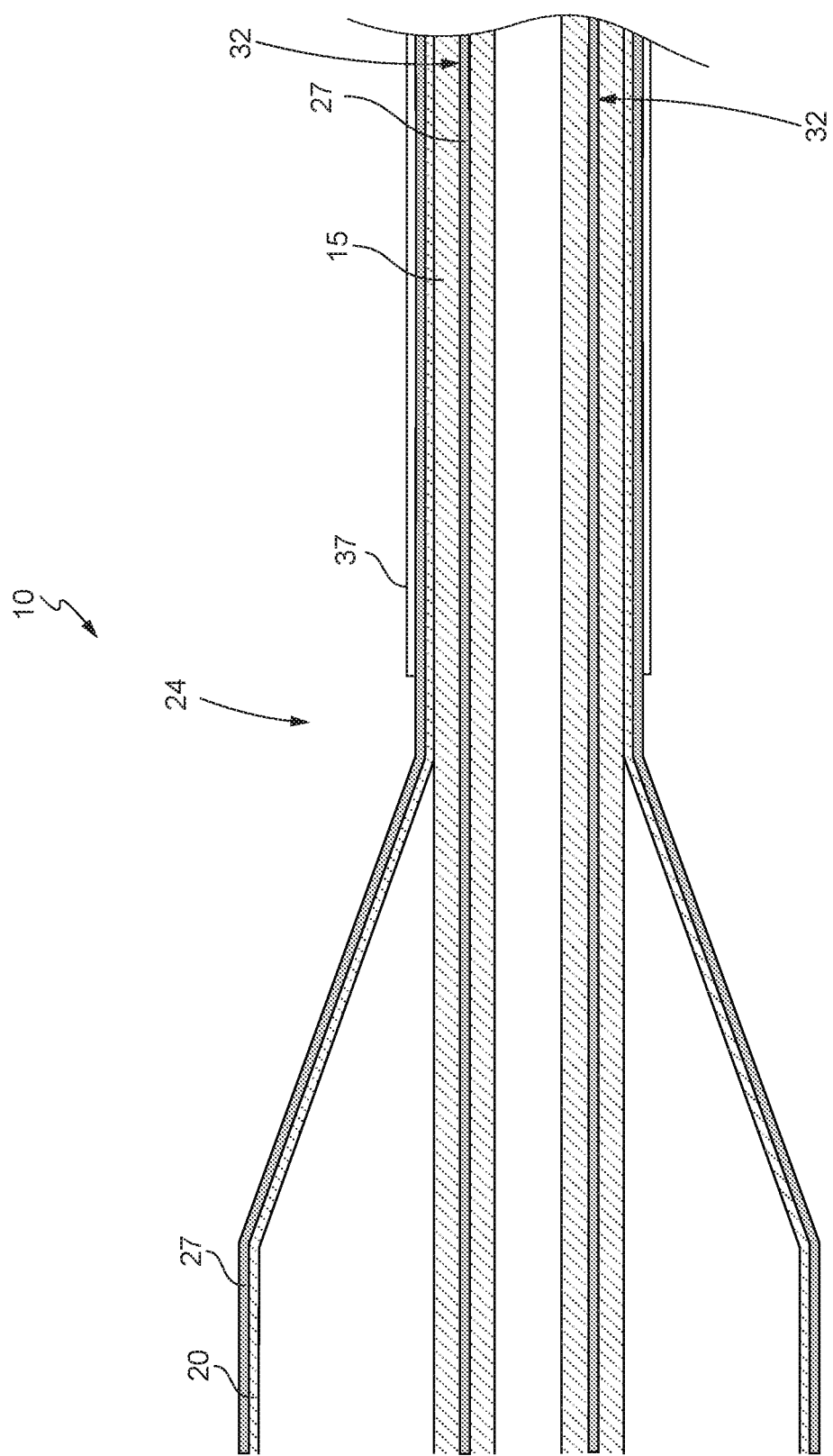
FIG. 4 is a side cross-sectional view of a proximal region of the expandable member assembly, in accordance with an embodiment of the disclosure.

FIG. 4 depicts a cross-sectional view of another portion of the medical device at the proximal end 24 of the expandable member 20. As shown in FIG. 4, the sheath 37 surrounds a portion of the cover 27 that extends along the length of the catheter 15. The cover 27 also surrounds the expandable member 20, as shown in FIG. 2. The length of the cover 27 that is inverted into the cover lumen 32 of the catheter 15 is also shown as extending within the cover lumen 32 along a length of the third section $S_3$ of the medical device along a length of the catheter 15. The inflation lumen 40 (shown in FIG. 3) is not visibly distinct from the guide wire lumen 38 in the cross-sectional view of FIG. 4.

Embodiments Including One or More Coatings

Figure 5A:
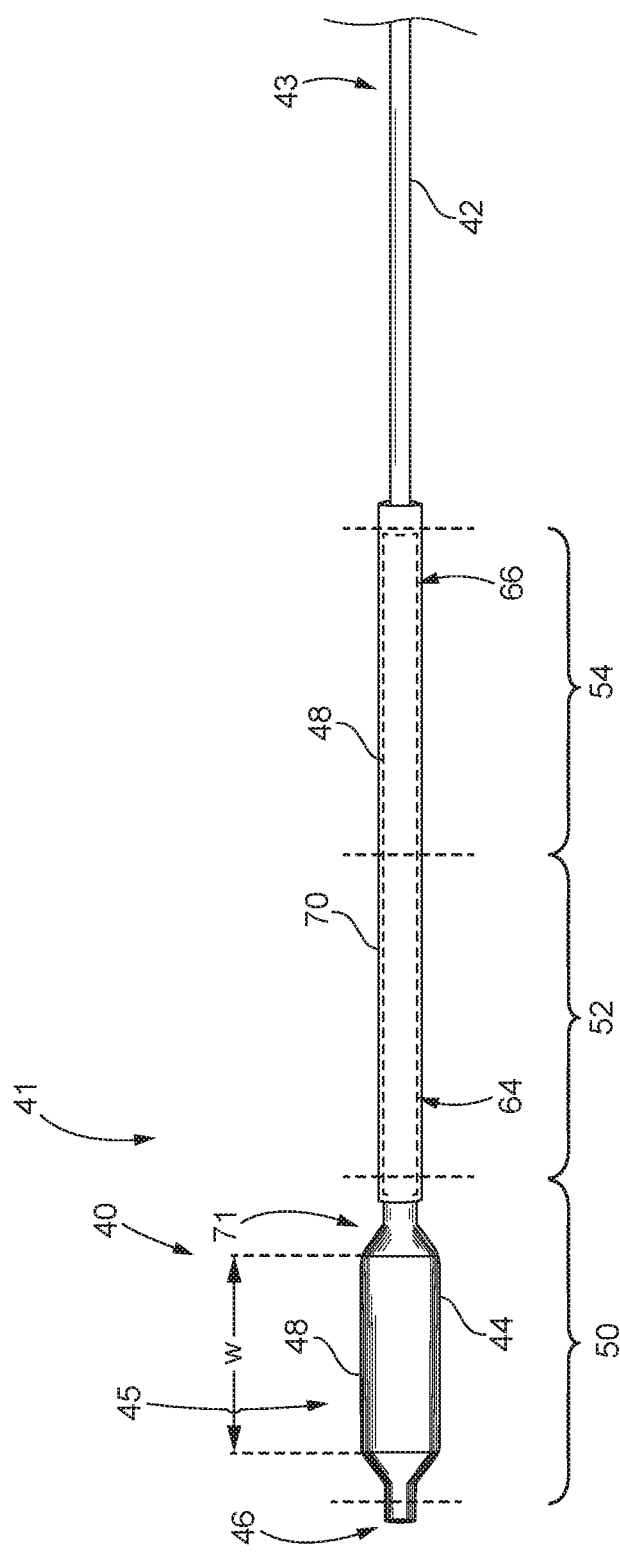
FIG. 5A is a side view of the expandable member assembly including a first region of a cover having a first coating or treatment surface disposed along the expandable member in an inflated state, in accordance with an embodiment of the disclosure.

FIG. 5A depicts an expandable member assembly 40 of a medical device 41, according to an embodiment of the present disclosure. The expandable member assembly 40 is positioned on a catheter 42 of the medical device 41. The expandable member assembly 40 includes an expandable member 44 positioned on a distal section 45 of the catheter 42. The expandable member assembly 40 also includes a cover 48 that is positioned around the expandable member 44 and which extends along a length of the catheter 42 towards a proximal end 43 of the catheter 42. The cover 48 comprises a first region 50, a second region 52, and a third region 54. In some embodiments, as shown in FIG. 5A, the first region 50, the second region 52, and the third region 54 can each have a length that is approximately equal to an overall length of the expandable member 44. In some embodiments, as shown in FIG. 5A, the first region 50, the second region 52, and the third region 54 can each have a length that is approximately equal to a working length (W) of the expandable member 44 at a nominal diameter, e.g., within 10% or within 20% of the working length. In some embodiments, one or more of the first, second, and third regions 50, 52, 54 can have a length that is greater than or less than the overall length of the expandable member 44.

An end of the cover 48 may be inverted into a cover lumen at a distal end 46 of the catheter 42. The cover 48 may be coupled to an actuator (not shown) of the medical device 41. The actuator may pull the end of the cover 48 positioned within the cover lumen from the distal end 46 of the catheter 42 to the proximal end 43 of the catheter 42 at various increments. In some embodiments, the cover 48 may be inverted into a proximal end 43 of the catheter 42 and pulled by the actuator to the distal end 43 of the catheter 42.

In some embodiments, one or more coatings may be positioned on an outer surface of the cover 48. The coatings may comprise one or more radiopaque elements and/or one or more therapeutic agents, for example therapeutic drug agents. In some embodiments, the coating may comprise a densified material positioned on the outer surface of the cover 48 that may increase a coefficient of friction of the surface of the cover 48. In some embodiments, one or more endoprosthesis may be positioned on the outer surface of the cover 48. In some embodiments, an endoprosthesis may be positioned between a region of the cover 48 that includes a pre-treatment (e.g., a therapeutic agent coating or a surface feature for removing plaque or other deposits from a lumen wall) and a region of the cover 48 that includes post-treatment (e.g. a therapeutic agent coating). In still yet other embodiments, one or more endoprosthesis may be positioned on an outer surface of the cover 48 along any length of the cover 48.

Therapeutic Agents

Therapeutic agents may include, but are not limited to: abciximab, acemetacin, acetylvismione B, aclarubicin, ademetionine, adriamycin, aescin, afromoson, akagerine, aldesleukin, am idorone, aminoglutethemide, amsacrine, anakinra, anastrozole, anemonin, anopterine, antimycotics, antithrombotics, thrombolytics such as tissue plasminogen activator (tPA), apocymarin, argatroban, aristolactam-All, aristolochic acid, arsenic and arsenic-containing oxides, salts, chelates and organic compounds, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, boswellic acids and their derivatives, bruceanoles A, B and C, bryophyllin A, busulfan, antithrombin, bivalirudin, cadherins, camptothecin, capecitabine, o-carbamoylphenoxyacetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-Type natriuretic peptide (CNP), cudxaisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, dunaimycin, epirubicin, epothilone A and B, erythromycine, estramustine, etoposide, everolimus, filgrastim, fluroblastin, fluvastatin, fludarabine, fludarabin-5'-dihydrogenphosphate, fluorouracil, folimycin, fosfestrol, gemcitabine, ghalakinoside, ginkgol, ginkgolic acid, glycoside 1 a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, bismuth and bismuth compounds or chelates, irinotecan, topotecan, hydroxycarbamide, miltefosine, pentostatine, pegaspargase, exemestane, letrozole, formestane, SMC proliferation inhibitor-2co, mitoxantrone, mycophenolate mofetil, c-myc antisense, b-myc antisense, [3-1apachone, podophyllotoxin, podophyllic acid-2-ethylhydrazide, molgramostim (rhuGM-CSF), peginterferon ct-2b, lanograstim (r-HuG-CSF), macrogol, selectin (cytokin antagonist), cytokin inhibitors, COX-2 inhibitor, NFkB, angiopeptin, monoclonal antibodies which inhibit muscle cell proliferation, bFGF antagonists, probucol, prostaglandins, 1-hydloxyl 1-methoxycanthin-6-one, scopolectin, NO donors, pentaerythiltol tetranitrate, syndxloimines, S-nitrosodeilvatives, tamoxifen, staurosporine, [3-oestradiol, ct-oestradiol, oestriol, oestrone, ethinyloestradiol, medroxyprogesterone, oestradiol cypionates, oestradiol benzoates, tranilast, kamebakaurin and other terpenoids, which are used in the treatment of cancer, verapamil, tyrosine kinase inhibitors (tyrphostins), paclitaxel, paclitaxel derivatives, 6-c-hydroxy paclitaxel, 2'-succinylpaclitaxel, 2'-succinylpaclitaxeltilethanolamine, 2'-glutarylpaclitaxel, 2'-glutarylpaclitaxeltilethanolamine, T-O-ester of paclitaxel with N-(dimethylaminoethyl) glutamide, T-O-ester of paclitaxel with N-(dimethylaminoethyl)glutamidhydrochloride, taxotere, carbon suboxides (MCS), macrocyclic oligomers of carbon suboxide, mofebutazone, lonazolac, lidocaine, ketoprofen, mefenamic acid, piroxicam, meloxicam, penicillamine, hydroxychloroquine, sodium aurothiomalate, oxaceprol, [3-sitosteiln, myrtecaine, polidocanol, nonivamide, levomenthol, ellipticine, D-24851 (Calbiochem), colcem id, cytochalasinA-E, indanocine, nocadazole, S 100 protein, bacitracin, vitronectin receptor antagonists, azelastine, guanidyl cyclase stimulator tissue inhibitor of metal proteinasel and 2, free nucleic acids, nucleic acids incorporated into virus transmitters, DNA and RNA fragments, plasminogen activator inhibitor-I, plasminogen activator inhibitor-2, antisense oligonucleotides, VEGF inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazole, enoxoparin, desulphated and N-reacetylated hepailn, tissue plasminogen activator, GpIIb/IIIa platelet membrane receptor, factor Xa inhibitor antibodies, hepailn, hirudin, r-hirudin, PPACK, protamine, prourokinase, streptokinase, warfarin, urokinase, vasodilators such as dipyramidol, trapidil, nitroprussides, PDGF antagonists such as triazolopyilmidine and seramine, ACE inhibitors such as captopril, cilazapill, lisinopill, enalapril, losartan, thioprotease inhibitors, prostacyclin, vapiprost, interferon a, [3 and y, histamine antagonists, serotonin blockers, apoptosis inhibitors, apoptosis regulators such as p65, NF-kB or Bcl-xL antisense oligonucleotides, halofuginone, nifedipine, tocopherol tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, naturally and synthetically obtained steroids such as inotodiol, maquiroside A, ghalakinoside, mansonine, strebloside, hydlocortisone, betamethasone, dexamethasone, non-steroidal substances (NSAIDS) such as fenoporfen, ibuprofen, indomethacin, naproxen, phenylbutazone and other antiviral agents such as acyclovir, ganciclovir and zidovudin, clotilmazole, flucytosine, griseofulvin, ketoconazole, miconazole, nystatin, terbinafine, antiprozoal agents such as chloroquine, mefloquine, quinine, furthermore natural terpenoids such as hippocaesculin, barringtogenol C21-angelate, 14-dehydloagrostistachin, agroskeiln, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N, and P, isodeoxyelephantopin, tomenphantopin A and B, coronailn A, B, C and D, ursolic acid, hyptatic acidA, iso-iildogermanal, cantenfoliol, effusantin A, excisaninA and B, longikauiln B, sculponeatin C, kamebaunin, leukamenin A and B, 13,18-dehydro-6-alphasenecioyloxychapariln, taxamaiiln A and B, regenilol, triptolide, cymarin, hydroxyanopterin, protoanemonin, chelibunrin chloride, sinococuline A and B, dihydronitidine, nitidine chloride, 12-beta-hydroxypregnadien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, cantansin, lycoridicin, margetine, pancratistatin, liilodenine, bisparthenolidine, oxoushinsunine, periplocoside A, ursolic acid, deoxypsorosperm in, psycorubin, ilcin A, sanguinailne, manu wheat acid, methylsorbifolin, sphatheliachromen, stizophyllin, mansonine, strebloside, dihydrousambaraensine, hydroxyusambailne, strychnopentamine, strychnophylline, usambarine, usambarensine, liriodenine, oxoushinsunine, daphnoretin, lariciresinol, methoxylailciresinol, sclerosant agents, syringaresinol, sirolimus (rapamycin), rapamycin combined with arsenic or with compounds of arsenic or with complexes containing arsenic, somatostatin, tacrolimus, roxithromycin, troleandomycin, simvastatin, rosuvastatin, vinblastine, vincilstine, vindesine, thalidomide, teniposide, vinorelbine, trofosfamide, treosulfan, tremozolomide, thiotepa, tretinoin, spiramycin, umbelliferone, desacetylvismioneA, vismioneA and B, zeoiln, fasudil.

The outer surface of the one or more regions 50, 52, 54 of the cover 48 may have a coating. In some embodiments, as shown in FIG. 5A, the first region 50 of the cover 48 may have no coating, the second region 52 of the cover 48 may have a coating 64, and the third region 54 of the cover 48 may have a coating 66. In some embodiments, the coating 64 may comprise a first therapeutic agent while the coating 66 may comprise a second therapeutic agent different than the first therapeutic agent. In use, the first region 50 of the cover 48 may be uncoated and may be positioned around the expandable member 44 for performing a typical angioplasty or other medical treatment prior to administering a therapeutic agent within the body lumen. In such an embodiment, the coating 64 on the second region 52 of the expandable member 44 may comprise paclitaxel, while the coating 66 on the third region 54 may comprise heparin. In some embodiments, the outer surface of one or more regions 50, 52, 54 of the cover 48 may have a coating and one or more regions 50, 52, 54 of the cover 48 may have an endoprosthesis. The coating on one or more of the regions 50, 52, 54 of the cover 48 may act as a pre-treatment (for application prior to positioning the endoprosthesis) or a post-treatment (for application after positioning the endoprosthesis).

In some embodiments, one or more regions 50, 52, 54 of the cover 48 may have the same coating. In some embodiments, one or more regions 50, 52, 54 of the cover 48 may have no coating. In embodiments in which one or more regions have the same coating, the dose of the coating may be different between the regions. For example, the coating 64 may comprise a therapeutic agent at a first dose, and the coating 66 of the third region 54 of the cover 48 may comprise the same therapeutic agent at a second dose different than the first dose. In some embodiments, the second dose may be greater than at least about 50% of the first dose. In some embodiments, the second dose may be approximately 90% of the first dose. In such embodiments, the expandable member 44 may be inflated at a first location with the second region 52 having the first dose of the therapeutic agent surrounding the expandable member 44. The expandable member 44 may be deflated and the cover 48 may be pulled through the cover lumen to position the third region 54 of the cover 48 having the second dose of the therapeutic agent positioned around the expandable member 44. The expandable member 44 may be reinflated at the same position to apply the second dose. In some embodiments, the expandable member assembly 40 may be repositioned at a different treatment site in the body prior to inflating the expandable member 44 with the third region 54 of the cover 48 around the expandable member to provide the therapeutic treatment at the different treatment site.

A sheath 70 may be positioned around a portion of the cover 48 along a length of the catheter 42 extending proximally from a proximal end 71 of the expandable member 44. The sheath 70 may protect the coatings 64, 66 positioned on the outer surface of the cover 48 during placement of the expandable member assembly 40 within the body lumen. The sheath 70 may comprise a polymer material or any other suitable material. The sheath 70 may be coupled directly to the catheter 42, for example via an adhesive. In some embodiments, the sheath 70 may be coupled to the hub of the medical device 41 or may be secured in place in other ways.

One or more coatings on the outer surface of the cover 48 may be administered into a body lumen in a particular order. For example, with reference to FIG. 5A the medical device 41 may be positioned within a body lumen and the expandable member 44 may be inflated at the treatment site with the first region 50 of the cover 48 surrounding the expandable member 44. The uncoated outer surface of the first region 50 of the cover 48 may be used to perform a typical angioplasty or other medical treatment within the body lumen. The expandable member 44 may later be deflated and the first region 50 of the cover 48 may be inverted into and pulled through the cover lumen of the catheter 42 such that the second region 52 of the cover 48 moves towards the distal end 46 of the catheter 42 and is positioned around the expandable member 44. The sheath 70 may protect the coatings 64, 66 on the second region 52 and the third region 54 of the cover 48 prior to deployment of the each respective region.

Figure 5B:
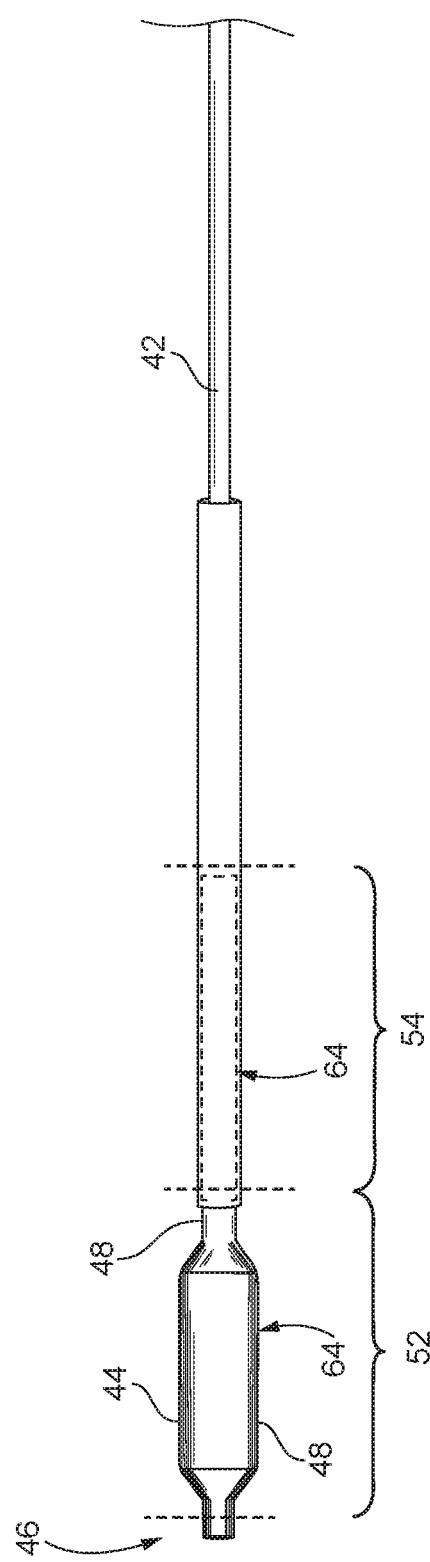
FIG. 5B is a side view of the expandable member assembly including a second region of the cover having a second coating or treatment surface disposed along the expandable member in an inflated state, in accordance with an embodiment of the disclosure.

As shown in FIG. 5B, the expandable member 44 can be reinflated with the second region 52 of the cover 48 positioned around the expandable member 44. Upon reinflation of the expandable member 44, the coating 64 on the outer surface of the second region 52 of the expandable member 44 may be administered to the body lumen at the treatment site. In some embodiments, the coating 64 on the second region 52 of the expandable member 44 may comprise paclitaxel. In some embodiments, the coating 64 may comprise a densified material. The densified material of the coating 64 may increase a coefficient of friction of a surface on which the coating 64 is positioned. The increased friction between the coating 64 and a wall of a vessel may shave plaque or other deposits from the wall of the vessel. The expandable member 44 may again be deflated, and the second region 52 of the cover 48 may be pulled through the cover lumen of the catheter 42 such that the third region 54, comprising coating 64, of the cover 48 moves towards the distal end 46 of the catheter 42 and is positioned around the expandable member 44.

Figure 5C:
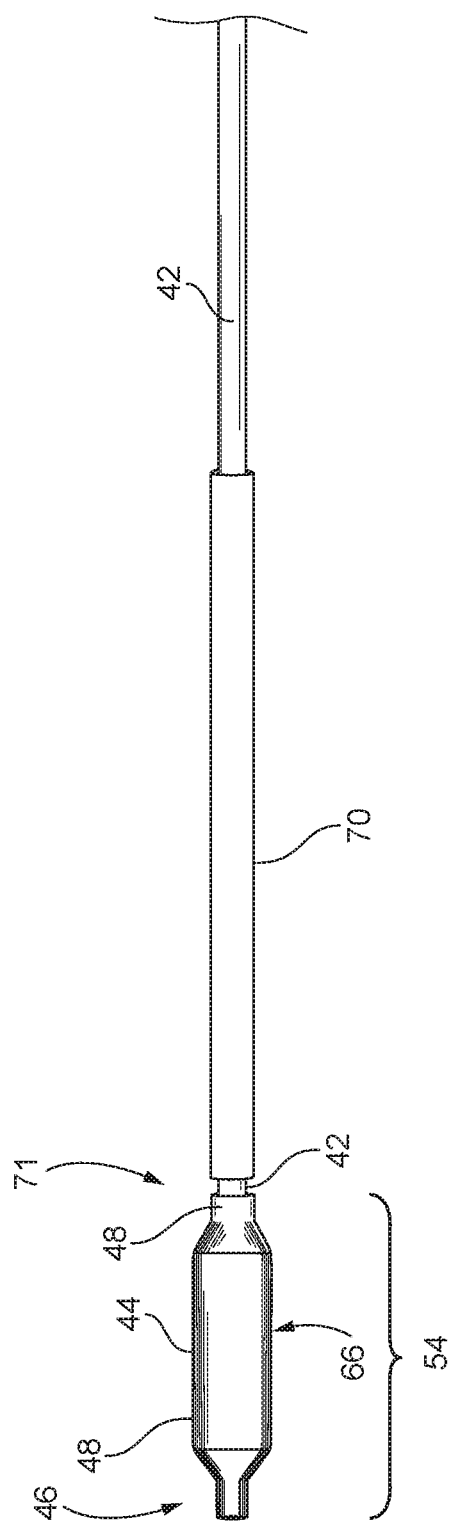
FIG. 5C is a side view of the expandable member assembly including a third region of the cover having a third coating or treatment surface disposed along the expandable member in an inflated state, in accordance with an embodiment of the disclosure.

As shown in FIG. 5C, as the second region 52 of the cover 48 is pulled through the cover lumen of the catheter 42 the third region 54 of the cover 48 moves towards a distal end 46 of the catheter 42 and is positioned around the expandable member 44. A portion of the catheter 42 may become exposed at the proximal end 71 of the expandable member 44 as the third region 54 of the cover 48 is moved into position around the expandable member 44. Upon reinflation of the expandable member 44, the coating 66 on the outer surface 60 of the third region 54 of the expandable member 44 may be administered to the body lumen at the treatment site. In some embodiments, the coating 66 on the third region 54 may comprise heparin.

In some embodiments of the present disclosure, the cover 48 may comprise greater or fewer regions. Moreover, the coatings 64, 66 on the surface of the cover 48 may be the same or different. Each of the coatings 64, 66 may be positioned on the outer surface 60 of the cover 48 without contacting one another. In some embodiments, a coating may be positioned on a surface of the first region 50 of the cover 48. In some embodiments, the sheath 70 may not be included. In some embodiments, one or more of the first, second, third, regions 50, 52, 54 of the cover 48 can have a length that is equal to or greater than a working length of the expandable member 44 when the expandable member 44 is inflated to a nominal diameter.

Embodiments with Varying Inflation Profiles

Figure 6A:
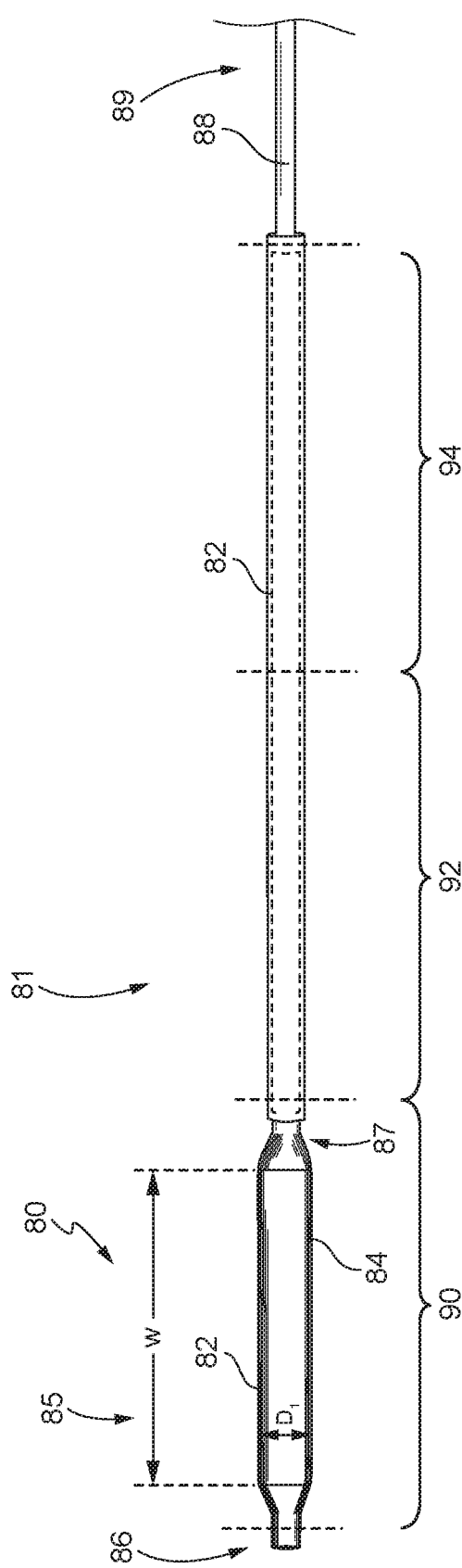
FIG. 6A is a side view of the expandable member assembly including a first region of the cover disposed along the expandable member in an inflated state at a first nominal diameter, in accordance with an embodiment of the disclosure.

FIGS. 6A-6C depict a medical device 81 comprising an expandable member assembly 80 and a catheter 88 according to an embodiment of the disclosure. The expandable member assembly 80 may include a cover 82 positioned around an expandable member 84 at a distal section 85 of the catheter 88. The cover 82 may also extend along a length of the catheter 88 beyond a proximal end 87 of the expandable member 84. In some embodiments of the present disclosure, the cover may not fully surround the expandable member 84 and/or the catheter 88. In some embodiments, the cover may comprise or may be coupled to lines (or strips of material at an end of the cover. The lines or strips of material may be attached to an actuator (not shown) that can pull the cover into and through the cover lumen. In some embodiments, as shown in FIGS. 6A-6C, the cover 82 is inverted into a cover lumen at a distal end 86 of the catheter 88, though in some embodiments the cover 82 may be inverted into the cover lumen at a proximal end 89 of the catheter 88. The end of the cover 82 that is inverted into the cover lumen at the distal end 86 of the catheter 88 can be coupled to an actuator (not shown) and be moved through the cover lumen along the length of the catheter 88 towards the proximal end 89 of the catheter 88.

As shown in FIG. 6A, the cover 82 can have a length that is multiple times greater than a working length (W) of the expandable member 84. The cover 82 may comprise ePTFE; for example, the cover may comprise an extruded ePTFE tube, a helical wrapped ePTFE tube, or a cigarette wrapped ePTFE tube. The cover 82 can include a first region 90, a second region 92, and a third region 94. In some embodiments, each of the first, second, and third regions 90, 92, 94 of the cover 82 can be substantially equal to the working length (W) of the expandable member 84. In some embodiments, one or more of the first, second, and third regions 90, 92, and 94 of the cover 82 can have a length that is approximately equal to an overall length of the expandable member 84. In some embodiments, one or more of the first, second, and third regions 90, 92, 94 of the cover 82 can have a length that is greater than or less than either the overall length of the expandable member 84 or the working length of the expandable member 84. In the embodiment shown in FIGS. 6A-6C the first, second, and third regions 90, 92, 94 each have a length that is approximately equal to the overall length of the expandable member 84, e.g., within 10% or 20% of the overall length.

One or more of the first, second and third regions 90, 92, 94 of the cover 82 may have varying nominal diameters. In some embodiments, the radial strength of the first, second and third regions 90, 92, 94 of the cover 82 can determine a nominal diameter of each of the regions of the cover 82. The cover 82 may comprise a single continuous material. In some embodiments, the cover 82 is comprised of a polymer having a node and fibril micro-structure. Refer to U.S. Pat. No. 3,962,153. A tube of such material can be placed onto a mandrel, longitudinally compressed and heat treated to preserve the compressed state (see, e.g., U.S. Pat. No. 5,308,664). The amount of longitudinal compression dictates the amount of radial strength. More longitudinal compression results in a higher degree of radial strength (i.e. the higher compression ratio). The first, second and third regions 90, 92, 94 of the cover can thereby have discrete zones with varying amounts of longitudinal compression (compression ratio) resulting in discrete zones of radial strength along the length of the cover. The varied radial strengths will then dictate the inflation profiles (e.g. the nominal diameters) of the expandable member over which the cover 82 is positioned.

In another embodiment, radial expansion may be dictated by helically wrapping a film and subsequently longitudinally compressing or necking the film to a reduced diameter. When the film is placed around a balloon and subsequently expanded, the film limits radial expansion. In some embodiments, the diameter of the film in an inflated profile (i.e. at a nominal diameter) may be determined by the necking of the film.

In some embodiments, one or more of the first, second and third regions 90, 92, 94 of the cover 82 may comprise a material that is resistant to distention. In such embodiments, one or more of the first, second and third regions 90, 92, 94 may have the same radial strength and may have varying nominal diameters defined by the diameter of the region. One or more of the first, second and third regions 90, 92, 94 may comprise one or more pleats or folds at a delivery configuration. The pleats or folds may unfurl as the respective regions expand to the nominal diameter.

Embodiments including a cover having discrete zones of radial strength according to the present disclosure can incorporate varying wall thicknesses and cross-sectional profiles. For example cover can have a circular, oval, triangular, square, rectangular or polygon cross-sectional shape at different regions along the length of a single cover. The cover can also incorporate wall sections of varying thickness. Various cross-sectional profiles and various wall thicknesses can be combined along the length of a single cover. Covers having discrete zones of radial strength according to the certain aspects can also incorporate lubricious coatings, drug eluting coatings, anti-microbial coatings, visualization aids or other additions that enhance the device function at various regions along the length of the cover.

In some embodiments, the radial strength of the cover 82 can vary between the first, second and third regions 90, 92, 94 of the cover 82. The cover 82 is positioned about the expandable member 84 and can limit the radial expansion of the expandable member 84 upon inflation to determine a nominal diameter of the expandable member 84. The varying radial strength of the first, second and third regions 90, 92, 94 can determine the nominal diameter of the expandable member 84 when each of the first, second and third region 90, 92, 94 are positioned over the expandable member 84.

In some aspects, the nominal diameter of the various regions (e.g., regions 90, 92, 94) of the a cover (e.g., cover 82) may be selected to deliver a particular endoprosthesis. In such embodiments, one or more endoprosthesis may be positioned along the various regions of the cover for deployment in a lumen of the body. The one or more endoprosthesis may have the same or varying lengths. In some embodiments, the one or more endoprosthesis may have the same or varying diameters that may correspond to the nominal diameters of the region of the cover on which each endoprosthesis is disposed.

FIG. 6A depicts the first region 90 of the cover 82 positioned around expandable member 84. The expandable member 84 and cover 82 has been inflated to a nominal $D_1$, the nominal diameter $D_1$ may be determined by the radial strength of the first region 90 of the cover 82 that overlays the expandable member 84. The nominal diameter $D_1$ can be, for example, between about 2 mm and about 4 mm, between about 2 mm and about 5 mm, or between about 2 mm and about 6 mm. In some aspects, the nominal diameter $D_1$ may be about 4 mm. The expandable member 84 may be deflated and the end of the cover 82 that is inverted into the cover lumen of the catheter 88 may be moved through the cover lumen towards the proximal end 89 of the catheter 88. As the first region 90 of the cover 82 is inverted into the cover lumen and moved towards the proximal end 89 of the catheter 88, the second region 92 of the cover 82 may be moved along the catheter 88 towards the distal end 86 and the second region 92 may be positioned around the expandable member 84.

As shown in FIG. 6B, the expandable member 84 may be reinflated with the second region 92 of the cover 82 around the expandable member 84. The radial strength of the second region 92 may be less than the radial strength of the first region 90 of the cover 82. The lower radial strength of the second region 92 may constrain the expandable member 84 to a nominal diameter $D_2$ that is greater than the nominal diameter $D_1$, optionally from 1 to 30% greater, e.g., from 1 to 10% greater. For example, the expandable member 84 may be constrained to a nominal diameter of between about 3 mm and about 4 mm, between about 3 mm and about 5 mm, or between about 3 mm and about 6 mm. In some aspects, the nominal diameter $D_2$ may be about 5 mm. The expandable member 84 may be deflated and the cover 82 may be pulled further through the cover lumen of the catheter 88 towards the proximal end 89 of the catheter 88. The cover 82 may be pulled through the cover lumen of the catheter 88 until the third region 94 of the cover 82 is positioned around the expandable member 84. The third region 94 of the cover 82 may have a lower radial strength than the second region 92 of the cover 82.

As shown in FIG. 6C, the expandable member 84 may be reinflated with the third region 94 of the cover 82 surrounding the expandable member 84. The radial strength of the third region 94 may be less than the radial strength of the second region 92 of the cover 82. The lower radial strength of the third region 94 may constrain the expandable member 84 to a nominal diameter $D_3$ that is greater than the nominal diameter $D_2$, optionally from 1 to 30% greater or from 1 to 10% greater. For example, the expandable member 84 may be constrained to a nominal diameter of between about 4 mm and about 5 mm, between about 4 mm and about 6 mm, or between about 4 mm and about 7 mm. In some aspects, the nominal diameter $D_3$ may be about 6 mm. Though three regions of the cover 82 are shown in FIGS. 6A-6C the cover 82 may include more or fewer regions. In some embodiments, the multiple regions of the cover 82 may have different inflation profiles, for example but not limited to different nominal diameters, different working lengths, and/or different inflation shapes. In still yet other embodiments, the multiple regions of the cover 82 may have different sequences of inflation along different portions of each of the regions 90, 92, 94 of the cover 82.

Various expandable member profiles can be derived by the use of a cover that has discrete zones of varying radial strength or varying nominal diameters along a portion of the cover overlaying the expandable member. In some embodiments of the present disclosure, the discrete zones of radial strength along a portion of the cover can dictate the expansion profile or sequence expansion of an underlying expandable member. In some embodiments, the cover may be configured to have a weak (or easy to expand) zone and at least one stronger (or harder to expand zone) along a portion of the cover overlaying the expandable member.

In some embodiments, an expandable member positioned under a region of the cover may initially inflate on one end (at a first pressure) and then progressively inflate along a length of the expandable member at higher pressures. A cover or a region of the cover can have 2, 3, 4, 5, 6, 7, 8, 9, 10 or more discrete zones of varying radial strength. The various discrete zones of radial strength can be arranged along a single region or multiple regions of the cover in any desired order. The radial strength of the discrete zones may also be individually tailored to expand with any desired pressure. The discrete zones of radial strength can be combined with non-expandable zones or with zones of very low radial strength. The controlled expansion profile or expansion sequence can be used to enable or improve various medical and industrial applications. In some embodiments, the inflation profile and/or sequences of inflation of a region of the cover 82 may be used for delivery of a specific endoprosthesis. In some embodiments, multiple endoprosthesis may be delivered using a single assembly having a cover comprising a plurality of regions. In some embodiments, the multiple endoprosthesis may be expanded via the same or different expansion profiles, with each expansion profile being determined by the portion of the cover on which the endoprosthesis is disposed. Each endoprosthesis may be positioned on a region of the cover having a desired expansion profile for the particular endoprosthesis disposed thereon.

Embodiments with Varying Surface Topographies

In some embodiments, an expandable member assembly of a medical device may have variable topographies. The topography of the expandable member assembly can affect the physical interaction between the expandable member assembly and the body or a device inside the body. The ability to control an expandable member assembly's topography, or three-dimensional surface characteristics, allows expandable member assemblies to interact with the body in new or improved modes. The expandable member assembly used inside the body may generally interact with the body through contact with an exterior surface of the expandable member of the expandable member assembly or in some embodiments with an exterior surface of the cover of the expandable member assembly.

In some embodiments, the expandable member assembly may have varied topographies and pre-configured surface textures defined by a region of the cover that is positioned around the expandable member. In some embodiments, the texture of the cover can vary along the length of the cover. For example, a textured network can comprise beads, filaments, fibers, rings, knits, weaves, and/or braids, which can be wrapped or otherwise disposed over or within a cover. The textured network creates raised surface patterns that can provide therapeutic effect. In some embodiments, the therapeutic effect can be provided to the wall of a lumen prior to deploying an endoprosthesis. In some embodiments, the therapeutic effect can be provided to the wall of the lumen after deploying an endoprosthesis. In some embodiments, a therapeutic effect can be provided both prior to and after deploying an endoprosthesis. The endoprosthesis may be deployed with the same assembly that provides the therapeutic effects without removal of the assembly from the lumen.

In some embodiments, a region of the cover comprises at least one aperture and a portion that is more resistant to deformation in a radial direction than the expandable member, either because cover comprises a less compliant material or has an upper distension limit that is less than the expandable member's upper distension limit. As such, the expandable member is configured to distend beyond the cover about the aperture at a given volume/pressure. In some embodiments, the cover can have a varied topography surface at various points along the length of the cover. In some embodiments, located within the aperture can be a therapeutic agent, preferably in a solid or viscous form. Upon inflation, the underlying expandable member will protrude through the aperture of the cover and convey the therapeutic agent external to the cover. In this manner, a therapeutic agent can be delivered to a surrounding tissue such as the intima of a vessel.

FIGS. 7A-7D depict a side view of a medical device 100 including an expandable member assembly 101 positioned on a catheter 106, according to an embodiment of the present disclosure. FIGS. 7A-7D illustrate the expandable member assembly 101 in various inflated states having a varied topography. The expandable member assembly 101 comprises expandable member 102 and cover 104. The expandable member 102 and the cover 104 may be attached to the catheter 106. The catheter 106 is in fluid communication with the expandable member 102, such that fluid can be introduced through catheter 106 into expandable member 102. The catheter 106 can be coupled to any suitable medical device, such as a syringe, an indeflator, pump or any other apparatus for conducting fluid through catheter 106 and into expandable member 102.

The cover 104 is disposed on an outer surface of the expandable member 102 and extends proximally from a proximal end 110 of the expandable member 102 along a length of the catheter 106 towards a proximal end 112 of the catheter 106. The cover 104 may have a length that is two, three, four or more times greater than an overall length of the expandable member 102. In some embodiments, the cover 104 may have a length that is two, three, four or more times greater than a working length of the expandable member 102 at a nominal diameter. The cover 104 may include a first region 114, a second region 116, and a third region 118 and terminates at a proximal end 109. Each of the first region 114, the second region 116, and the third region 118 of the cover 104 may extend along the expandable member 102 and along a length the catheter 106 beyond the proximal end 110 of the expandable member 102.

The first, second, and third regions 114, 116, 118 of the cover 104 may have different characteristics as shown in FIGS. 7A-7D. A sheath 119 may surround at least a portion of the second region 116 and third region 118 of the cover 104. In some embodiments, the sheath 119 may protect a coating on a surface of the cover 104. In some embodiments, the sheath 119 may retain a portion of the cover 104 at a desired diameter, for example the sheath 119 may retain the second and third region 116, 118 of the cover 104 at the desired diameter that is smaller than a delivery diameter of the second and third regions 116, 118 of the cover 104.

Figure 7A:
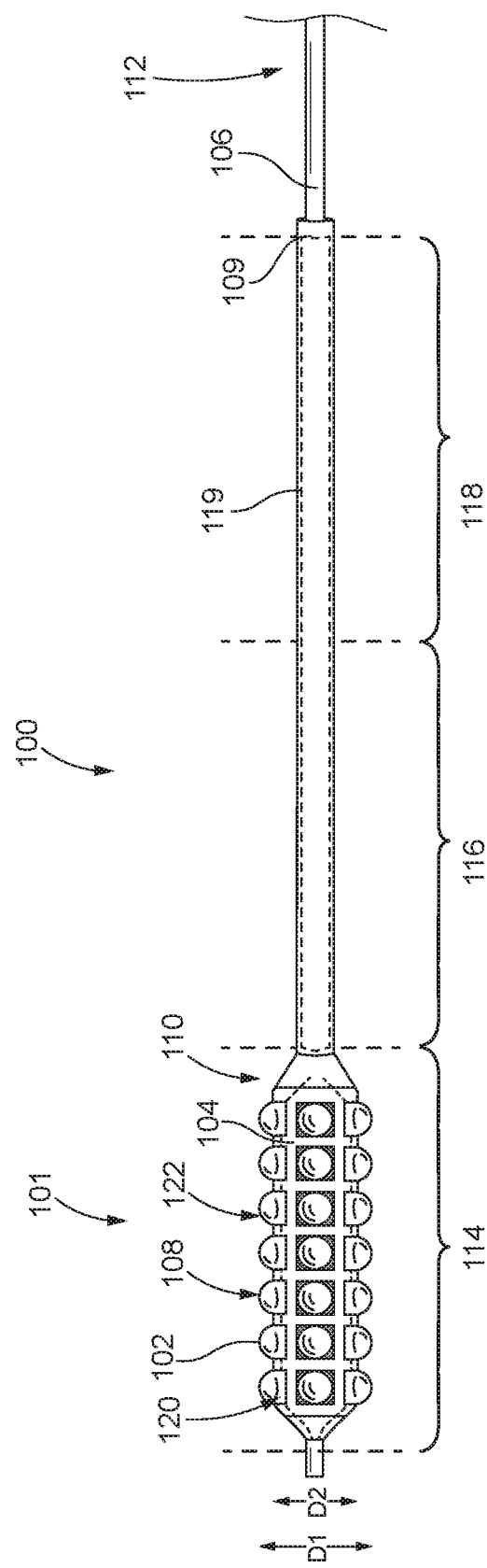
FIG. 7A is a side view of the expandable member assembly including a first region of the cover having apertures disposed along the expandable member in an inflated state, in accordance with an embodiment of the disclosure.

As shown in FIG. 7A, the first region 114 of the cover 104 can comprise at least one aperture 120. The first region 114 of the cover 104 can constrain a region of expandable member 102 during inflation. The restraining action of first region 114 of the cover 104 causes expandable member 102 to distend at apertures 120 in the first region 114 of the cover 104. As shown in FIG. 7A, the portions of the expandable member 102 distending through the apertures 120 of the first region 114 of the cover 104 has a diameter shown as "D1." The first region 114 of the cover 104 positioned over the expandable member 102 has a diameter of "D2," as shown in FIG. 7A. Apertures 120 can comprise an opening or weakened site in the first region 114 of the cover 104. In this regard, an opening can be a hole, cut, or any other discontinuous section of the material of the first region 114 of the cover 104. For example, a hole could be formed by puncturing first region 114 of the cover 104. Alternatively, apertures 120 can comprise an area of first region 114 where a region of the material has been removed or otherwise weakened such that the weakened region at least partially deforms or detaches in response to inflation of expandable member 102 and permits distension beyond the first inflated state. Apertures 120 can be formed by any suitable means, including cutting, stamping, laser cutting, perforating, and/or punching/puncturing and/or the like. In various embodiments, the first region 114 of the cover 104 can comprise a net like structure.

In some embodiments, a therapeutic agent may be disposed on an inner or outer surface of the expandable member 102 or portion of the cover 104, or inside the expandable member 102. For example, a coating comprising a therapeutic agent may be coated on an outer surface 108 of the expandable member 102. As the expandable member 102 protrudes through the apertures 120 the therapeutic agent can be released at a localized portion of the body lumen. The therapeutic agent can comprise a liquid or solid form. Liquid form can be of a desired viscosity suitable for the treatment desired. In some embodiments, the expandable member assembly 101 can also have a coating comprising a therapeutic agent disposed on, inside of, temporarily filling, or otherwise be integrated with one or more of the first region 114, second region 116, and third region 118 of the cover 104.

The expandable member 102 can comprise any suitable compliant expandable member. As described above, a compliant expandable member can comprise a polymeric material. Exemplary materials for a compliant expandable member include elastomers such as polyurethane and silicone, natural rubber or latex products, synthetic rubber such as nitrile butadiene, or other synthetic or naturally occurring polymeric materials. In various embodiments, expandable member 102 may not be fully compliant, but is more compliant than first region 114 of the cover 104 and is sufficiently flexible to inflate to a diameter larger than the diameter of the restraining first region 114 at a given pressure, and thereby produces protrusions 122 of the expandable member 102. Thus, a semi-compliant or non-compliant expandable member can be used. Optionally, the first region 114 of the cover 104 can comprise apertures that vary in size. Increasing the size the apertures can allow for a wider (or "coarser") protrusion. By combining varying aperture sizes with a tapered cover profile the "scraping" effect of the assembly can be intensified proximally to distally or vice versa due to the different protrusion heights of the expandable member 102.

In some embodiments of the disclosure, the first region 114 of the cover 104 can comprise a wall having regions of reduced or less compliance than other, more distensible regions of wall. The other regions being essentially the "apertures" that permit the underlying expandable member 102 to expand outwardly relative to the regions of reduced or less compliance of the first region 114 of the cover 104. The more distensible regions can comprise an upper distension limit. The regions of reduced compliance can be formed through laser densification or by imbibing with a polymer that reduces the compliance in the imbibed region. In an embodiment, the regions of reduced compliance have substantially the same thickness as the more distensible regions. Similarly, with other embodiments described herein, the first region 114 of the cover 104 can be formed via tape wrapping or extrusion and can comprise ePTFE or any other material wherein the compliancy can be varied at discrete sites.

In various embodiments of the present disclosure, the first region 114 of the cover 104 can comprise any size-limited form that acts to constrain the expandable member 102 along the points of contact. Alternatively, the first region 114 of the cover 104 can comprise a form less compliant than the expandable member 102 so that the expandable member 102 is constrained along the points of contact. As such, the first region 114 of the cover 104 may be constructed of any material that cannot be appreciably deformed beyond a first inflated state during inflation of the expandable member 102.

With the described components, one can adapt the compliance of at least a portion of the cover and/or adapt an aperture pattern along at least a portion of the cover to control the topography of an expandable member assembly. For example, an aperture pattern can comprise many small apertures to obtain a "fine texture" pattern or can comprise fewer larger openings to obtain a more "coarse texture" pattern. As one can appreciate, any possible aperture pattern, or combinations of aperture patterns, is contemplated herein. For example, a first region of a cover can comprise a square grid like aperture pattern and a second region of the cover can comprise a diamond shaped pattern.

In other embodiments of the present disclosure, an expandable member expanding through a cover can define ridges and troughs which, for example, run parallel to the longitudinal axis of the expandable member. In one embodiment, these provide for blood perfusion between expandable member and vessel wall during a treatment when the expandable member is expanded. In some embodiments, the first region 114 of the cover 104 may not include apertures 120. In some embodiments, the first region 114 of the cover 104 may only include a therapeutic agent coating, for example but not limited to a drug coating.

Figure 7B:
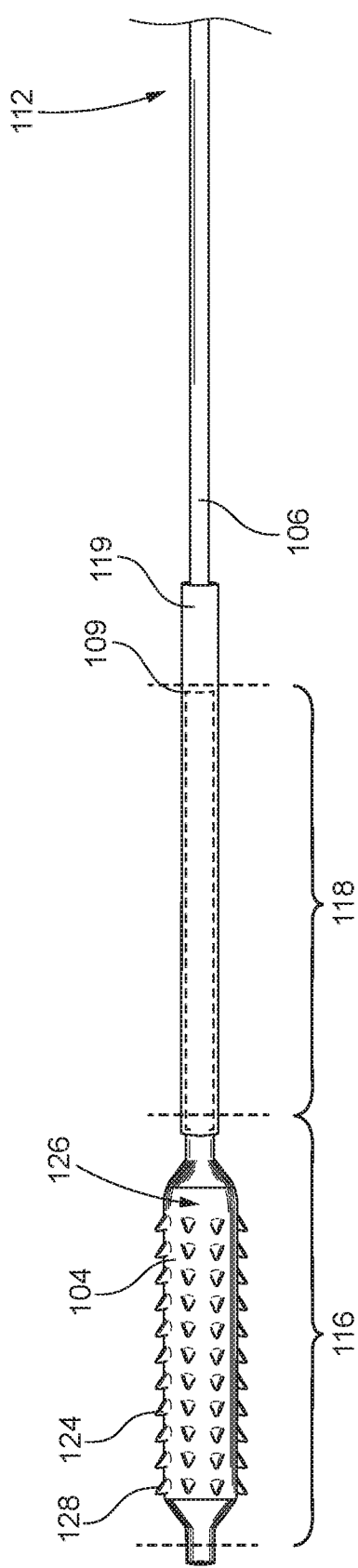
FIG. 7B is a side view of the expandable member assembly including a second region of the cover having scores disposed along the expandable member in an inflated state, in accordance with an embodiment of the disclosure.

FIG. 7A depicts the first region 114 of the cover 104 surrounding the expandable member 102 at an inflated profile. As shown in FIG. 7B, the expandable member 102 can be deflated and the first region 114 of the cover 104 can be inverted into a cover lumen of the catheter 106 and pulled toward the proximal end 112 of the catheter 106 by an actuator (not shown). As the first region 114 of the cover 104 is pulled through the cover lumen of the catheter 106 the second region 116 of the cover 104 is moved from its position around the catheter 106 and becomes positioned around the expandable member 102. The second region 116 of the cover 104 may have a different surface topography than the first region 114 of the cover 104.

In some embodiments, as depicted in FIG. 7B, the second region 116 of the cover 104 may include a plurality of scored portions 124. Upon inflation, as illustrated in FIG. 7B, the scored portions 124 will partially separate from a surface 126 of the cover 104 and will form an outwardly extending protrusion. The ruptured portions of cover 104 that is created by the rupture of scores 124 forms apertures 128 in which the expandable member 102 can be at least partially exposed. In various embodiments, one or more of the scores 124 can be formed as a through cut in the material of the second region 116 of the cover which would not have to rupture to achieve the desired effect.

Scoring and later rupturing of scores can enable the insertion of sharp objects into the body in a substantially unsharpened state and then provide for the deployment of the sharp object at a particular time. In addition, scoring and later rupturing can aid in the delivery of therapeutic agents. For example, a therapeutic agent can be disposed between the expandable member 102 and the second region 116 of the cover 104. The cover 104 can seal the therapeutic agent over the expandable member 102 such that when placed into the body, the therapeutic agent is substantially retained in a space between the expandable member 102 and the cover 104. Upon rupture of a scored portion 124 of the cover 104, the therapeutic agent can be released into a localized portion of the body. In some embodiments, the second region 116 of the cover can remove plaque and/or other deposits from a wall of the lumen. In some embodiments, a therapeutic coating may have been applied to the wall of the lumen by the first region 114 prior to removing the plaque and/or other deposits from the wall with the scored portions 124 of the second region 116 of the cover 104, without having removed the medical device 100 from the lumen.

Figure 7C:
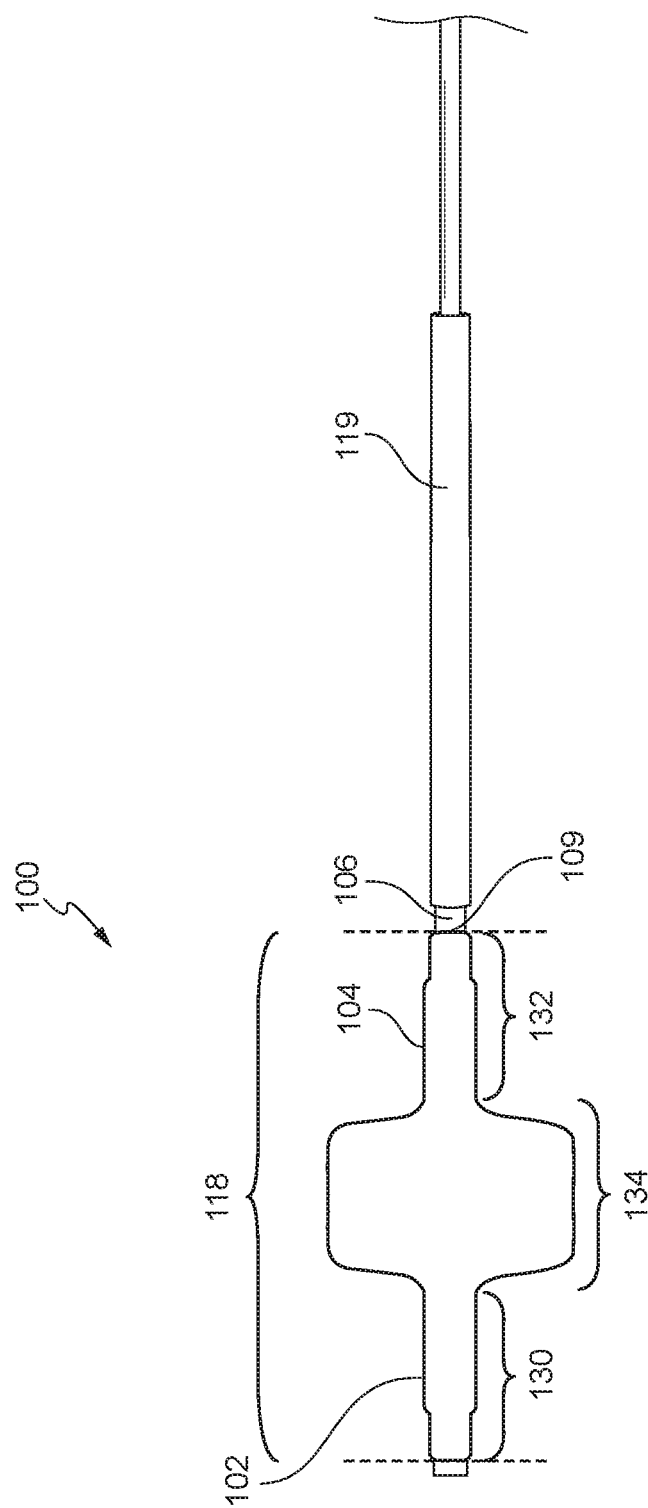
FIG. 7C is a side view of the expandable member assembly including a third region of the cover disposed along the expandable member in a first inflated state, in accordance with an embodiment of the disclosure.

The expandable member 102 can be deflated and the second region 116 of the cover 104 can be pulled through the cover lumen of the catheter 106. As the second region 116 inverts into the catheter 106 and is moved towards the proximal end 112 of the catheter, the third region 118 of the cover 104 can be moved from under the sheath 119 to surround the expandable member 102 (shown in FIG. 7C). As shown in FIG. 7A as compared to FIG. 7C, the proximal end 109 of the cover 104 is now positioned closer to the expandable member 102 as the cover 104 has moved. In some embodiments, as shown in FIG. 7C the third region 118 of the cover 104 can comprise a varied radial strength along the length of the third region 118 of the cover 104 to define a sequence of inflation of the third region 118 when positioned on the expandable member 102. A first end 130 and a second end 132 of the third region 118 can comprise a higher radial strength, or a different nominal diameter, than a middle portion 134 of the third region 118.

As the underlying expandable member 102 is inflated, the middle portion 134 of the third region 118, having a lower radial strength, can expand and thus permit the expandable member 102 to expand while the first and second ends 130, 132 of the third region 118 are constrained at a smaller diameter and thereby constrain the expandable member 102 at the smaller diameter. When the expandable member 102 is inflated to a greater pressure, the first and second ends 130, 132 of the third region 118 of the cover 104 can expand, permitting the expandable member 102 to also expand, to an inflated as shown in FIG. 7D.

Figure 7D:
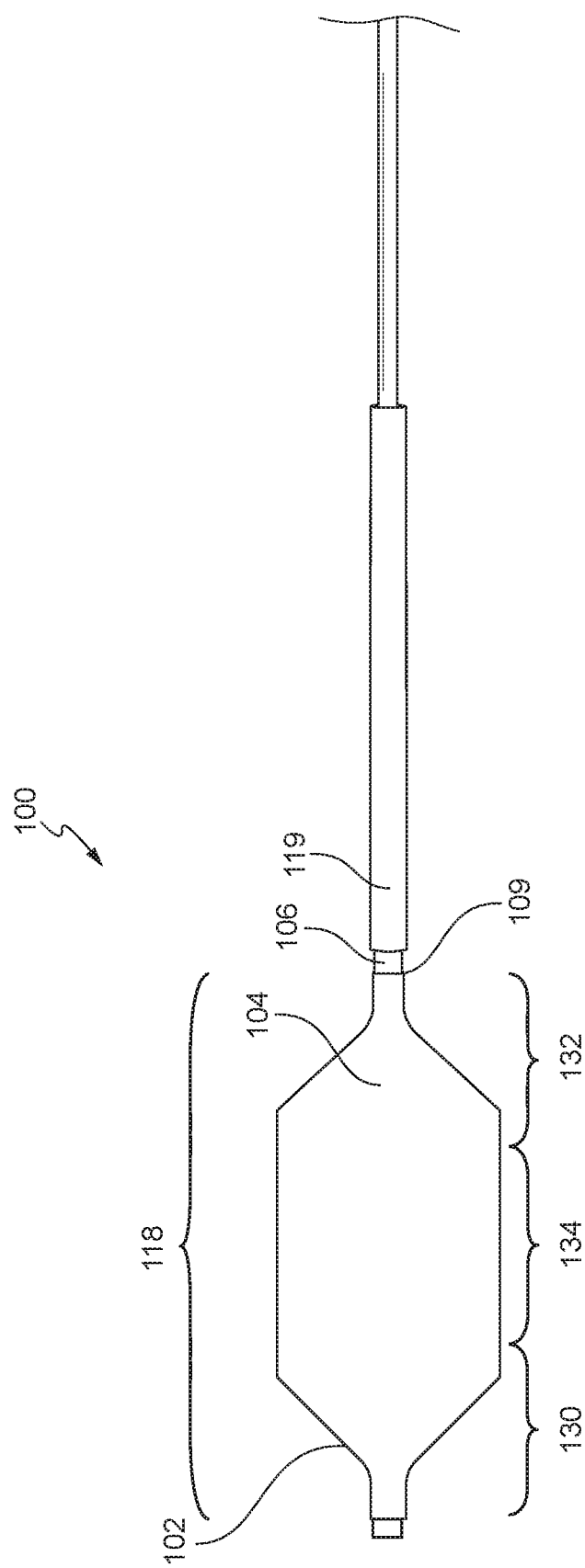
FIG. 7D is a side view of the expandable member assembly including the third region of the cover disposed along the expandable member in a second inflated state, in accordance with an embodiment of the disclosure.

As shown in FIGS. 7C-7D the expandable member 102 underlying the third region 118 of the cover 104 can initially expand to a nominal diameter at the middle portion 134 of the third region 118, as the pressure is increased the expandable member 102 can expand to the nominal diameter at the first and second ends 130, 132 of the third region 118. The expansion sequence shown in FIGS. 7C and 7D can be used to enable or improve various medical and industrial applications. For example, stents that are easily longitudinally compressed during expansion can be expanded by the expandable member and cover described in accordance with embodiments of the present disclosure. The stent can be expanded from the center out, thus maintaining the stent longitudinally tensioned as it is expanded. An example of such a stent is described in U.S. Patent Application Publication U.S. 2009/0182413. The longitudinal tension prevents the stent from being longitudinally compressed. The cover can be configured to control the sequence of expansion of the underlying expandable member to inflate in the sequence according to the type of stent, the size of the stent, or other stent characteristics that may define the inflation sequence desired for the stent to be delivered. In some embodiments, multiple regions of the cover may be configured to deliver a particular stent. In some embodiments, the cover may be configured to deliver multiple stents that are the same type of stent via the varied regions of the cover. In some embodiments, the various regions of the cover may be configured to deliver multiple different stents.

In other embodiments, the radial strength of the portions of the third region 118 can differ from the embodiment shown in FIGS. 7C and 7D to dictate a different expansion profile or sequence of an underlying (or overlying) expandable element. For example, in some embodiments, an opposite configuration of the third region 118 of the cover 104 can cause the expandable member 102 to expand from the ends 130, 132 in towards the middle portion 134 and thereby compress the overlaying device. A heart valve stent may require a stent that is expanded in a specific "hour-glass" shape, wherein the hour-glass shape is developed in a specific sequence. In other applications the expansion can begin at one end and progress to the opposing end of the expandable member 102, thereby creating a "pushing" or peristaltic motion. In some embodiments, a coating may be positioned on one or more of the first region 114, second region 116, and the third region 118. The coating may comprise a therapeutic agent, examples of therapeutic agents are provided below the heading "Therapeutic Agents" above.

In some embodiments of the present disclosure, one or more of the regions of a cover can also impact the general profile of an expandable member over which the cover is positioned. For example, at a first inflated state with a first region of the cover positioned about the expandable member assembly can have a diameter that is larger or smaller at different locations along the expandable member, for instance to form a taper. Thus, while expandable member can inflate in the shape of a cylinder, one of the regions of the cover can have a non-cylindrical shape, and this non-cylindrical shape can be the general profile of expandable member assembly when the expandable member is inflated with the region of the cover having the non-cylindrical shape. Such a generally tapered profile can be used to better conform to cardiovascular vessel diameters which change over length, for example. In addition, the lesion or thrombus "scraping" effect of the expandable member assembly can be intensified proximally to distally or vice versa due to the varying profile dimensions.

Figure 8A:
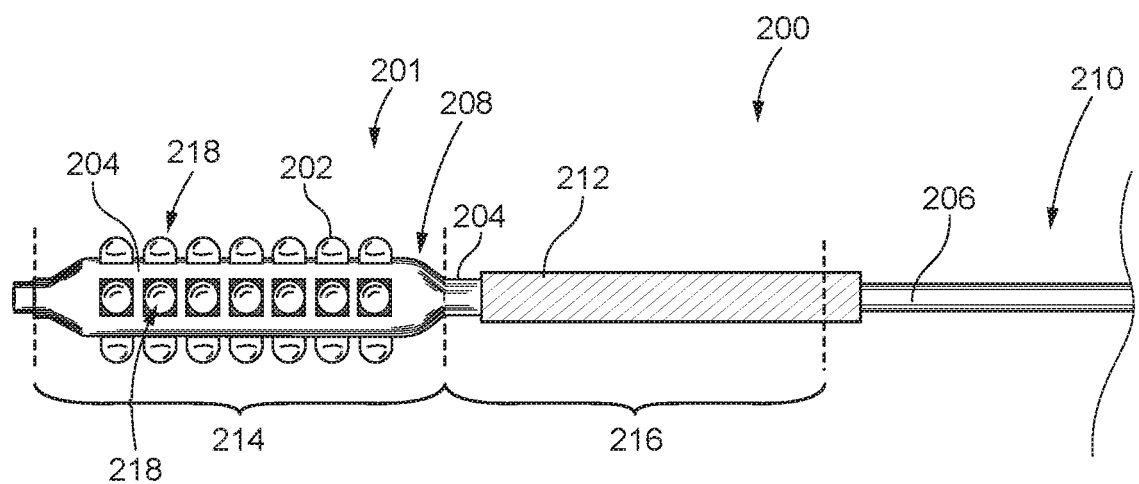
FIG. 8A is a side view of an expandable member assembly including a first region of the cover having apertures disposed along an expandable member in an inflated state, in accordance with an embodiment of the disclosure.
Figure 8B:
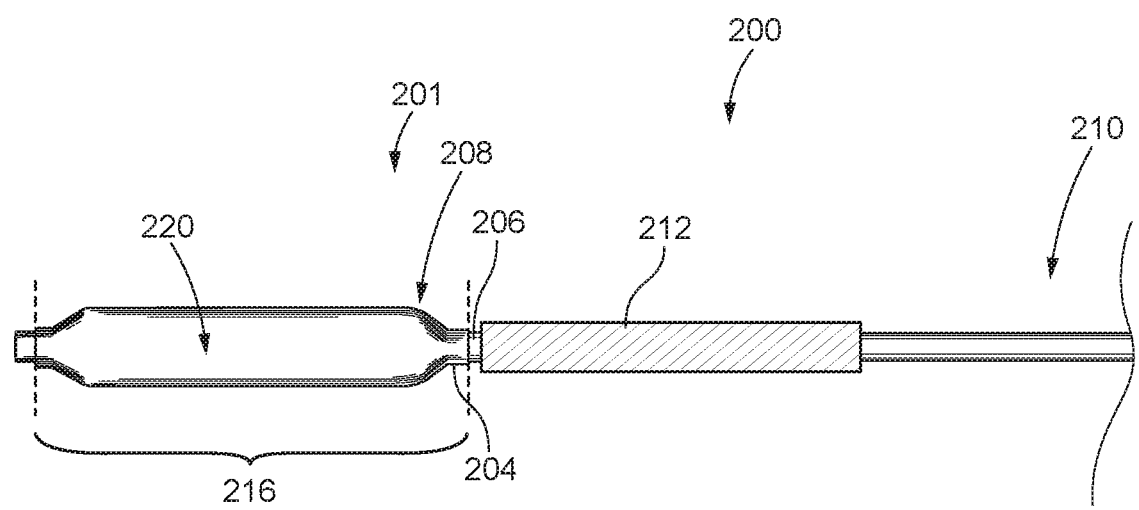
FIG. 8B is a side view of the expandable member assembly including a second region of the cover having a coating disposed along the expandable member in an inflated state, in accordance with an embodiment of the disclosure.

FIGS. 8A-8B depicts a medical device 200 including an expandable member assembly 201 according to an embodiment of the disclosure. The expandable member assembly 201 includes a cover 204 overlaying an expandable member 202. The medical device 200 can include a catheter 206 to which the expandable member 202 and the cover 204 are attached. The catheter 206 may be in fluid communication with the expandable member 202, such that fluid can be introduced through catheter 206 into expandable member 202. The cover 204 is disposed on an outer surface of the expandable member 202 and extends beyond a proximal end 208 of the expandable member 202 along a length of the catheter 206 towards a proximal end 210 of the catheter 206. The cover 204 may have a length that is two, three, four or more times greater than a working length of the expandable member 202 at a nominal diameter. A sheath 212 may be disposed about at least a portion of the cover 204 that extends along the catheter 206.

The cover 204 may include a first region 214 and a second region 216. In some embodiments, the cover 204 may include more or fewer regions. The first region 214 and the second region 216 may have different characteristics, including varied nominal diameters, varied surface topographies, and/or varied coatings. In the embodiment of the presented disclosure shown in FIGS. 8A-8B, the first region 214 of the cover 204 may include apertures 218. The first region 214 of the cover 204 can constrain a region of expandable member 202 during inflation. The restraining action of first region 214 of the cover 104 causes the expandable member 202 to distend through the apertures 218 in the first region 214 of the cover 204.

During treatment of a lesion, the expandable member assembly 201 may be inflated at a treatment site. The expandable member assembly 201 may be inflated with the first region 214 of the cover 204 positioned around the expandable member 202. After treating the treatment site with the textured surface of the expandable member assembly 201 defined by the first region 214 and the expandable member 202, the expandable member 202 may be deflated. The cover 204 may be pulled through a cover lumen in the catheter 206 and moved through the cover lumen towards the proximal end 210 of the catheter 206. As the first region 214 of the cover 204 is pulled off the expandable member 202 and through the cover lumen, the second region 216 of the cover 204 is pulled from under the sheath 212 and moved in position around the expandable member 204. The second region 216 of the cover 204 may include a coating 220. The coating 220 may comprise a therapeutic agent. The coating 220 may be protected by the sheath 212 during the initial placement of the expandable member assembly 201 at the treatment site and during deployment of the expandable member assembly 201 with the first region 214 positioned around the expandable member 202.

As shown in FIG. 8B, with the second region 216 of the cover 204 positioned around the expandable member 202, the expandable member 202 may be reinflated. In the inflated state shown in FIG. 8B, the coating 220 on the second region 216 of the cover 204 may contact and be transmitted to the treatment site upon inflation of the expandable member 202 with the second region 216 of the cover 204 positioned about the expandable member 202.

In some embodiments of the present disclosure, the first region 214 and the second region 216 may have different characteristics than those shown in FIGS. 8A, 8B. For example, one or both of the first region 214 and the second region 216 may provide for a different surface topography than shown in the figures, a specific sequence of inflation (e.g., inflating from the middle region outwards to the end of the expandable member), a specific inflation shape (e.g., a consistent diameter along a working length of the expandable member), or other characteristics related to the inflation profile of the expandable member assembly. In some embodiments, one or both of the first region 214 and the second region 216 of the cover 104 may also include a coating that includes a therapeutic agent, a hydrophilic coating, a hydrophobic coating, or other suitable coatings for an expandable member assembly. Various combinations of therapeutic agents, textures, inflation profiles, and endoprosthesis may be used on the regions 214, 216 of the cover 104.

Figure 10A:
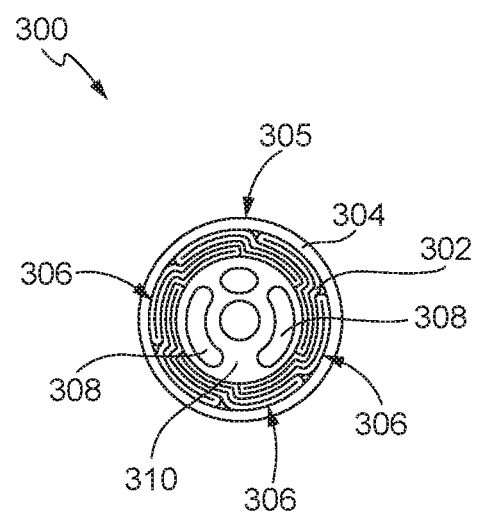
FIG. 10A is a cross-sectional front view of a medical device that includes an expandable member in a first inflated position, in accordance with an embodiment of the disclosure.
Figure 10B:
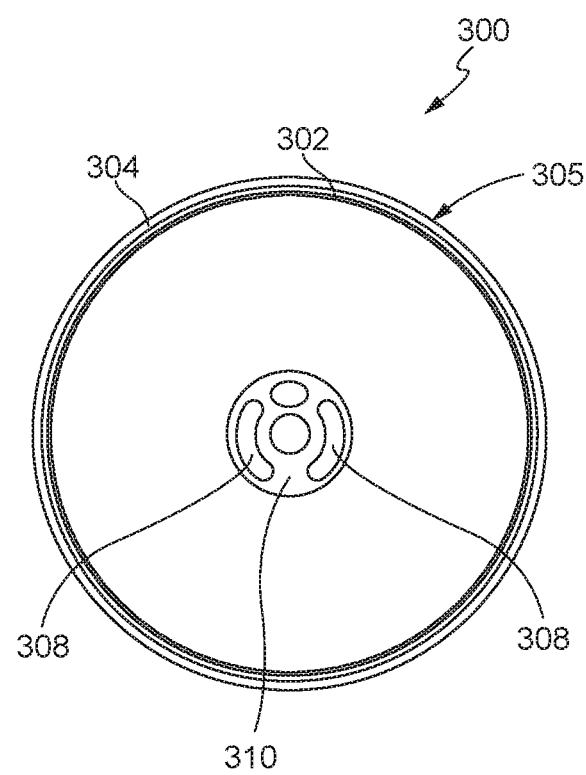
FIG. 10B is a cross-sectional front view of the medical device with the expandable member in a second inflated position, in accordance with an embodiment of the disclosure.

FIGS. 10A and 10B show a cross-sectional front-view of a portion of an expandable member assembly 300 of a medical device according to an embodiment of the present disclosure. The expandable member assembly 300 includes an expandable member 302 and a cover 304. FIG. 10A shows the expandable member 302 in an uninflated state and FIG. 10B shows the expandable member 302 in a partially inflated state. The cover 304 may include two or more regions. Each of the two or more regions of the cover 304 may have different characteristics. For example, a first region 305 of the cover 304 overlaying the expandable member 302 in FIGS. 10A and 10B may comprise a radial strength or other characteristic configured to control the diameter of the cover 304 and thereby the diameter of the underlying expandable member 302 as the expandable member 302 is inflated. As shown in FIG. 10A the expandable member 302 in a deflated or partially inflated configuration may include pleats or wings 306. Thought two wings 306 are shown in FIG. 10A, in some embodiments more or fewer wings may be used, for example but not limited to 5 or 6. In some embodiments the pleats or wings 306 may be oriented along a longitudinal axis of the expandable member 302, in other embodiments the pleats or wings 306 may be oriented along an axis that is perpendicular to the longitudinal axis. As the expandable member 302 inflates, the wings 306 may unfold. The torsional stress of the unfolding wings 306 can impart a force or stress on the wall of the vessel in which it is deployed. The first region 305 of the cover 304 overlaying the expandable member 302 may control the expansion of the expandable member 302 and may prevent the wings 306 from imparting a potentially damaging stress on the vessel wall as wings 306 unfold. In some embodiments, another region (not shown) of the cover 304 may comprise different characteristics, for example but not limited to a coating, a different radial strength, or a different surface topography. Another region of the cover 304 (not shown) may be positioned around the expandable member 302 before or after the first region 305 and may comprise different characteristics than that of the first region 205. For example, the other region of the cover 304 may include a coating, a surface topography, varied radial strength along the length of the other region, a different coefficient of friction on the surface of the other region, or other characteristics. The cover 304 may be inverted into a cover lumen 308 of a catheter 310 and moved along the longitudinal axis of the catheter 310 to position the other region of the cover 304 over the expandable member 302. In some embodiments, the cover 304 may include additional regions having the same or different characteristics as the other regions of the cover 304.

Figure 11:
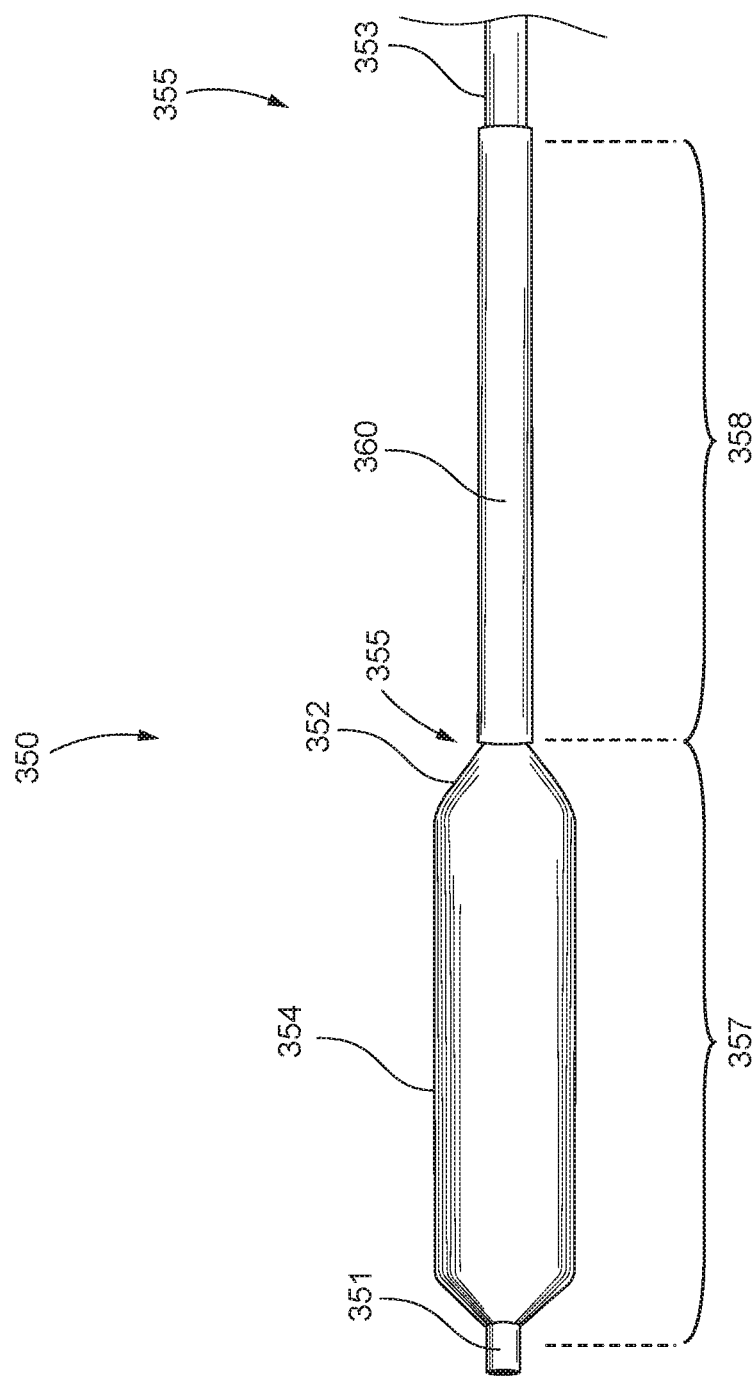
FIG. 11 is a side view of an expandable member assembly including a first region of the cover about the expandable member, in accordance with an embodiment of the disclosure.

FIG. 11 depicts a side view of a medical device that includes an expandable member assembly 350 and a catheter 353 according to an embodiment of the disclosure. The expandable member assembly 350 includes a cover 352 positioned around at least a portion of an expandable member 354. The cover 352 also extends beyond a proximal end 355 of the expandable member 344 along a length of the catheter 353 towards a proximal end 355 of the catheter 353.

The cover 352 can include a first region 357, shown in FIG. 11 as surrounding the expandable member 354. The cover 352 also includes a second region 358 that extends along a length of the catheter 353. Each of the first region 357 and the second region 358 can have a length that is approximately equal to an overall length of the expandable member 354, in some embodiments one or more of the first region 357 and the second region 356 may have a different length. A sheath 360 is positioned around at least a portion of the second region 358 of the cover 352. The sheath 360 can comprise a polymer material or other suitable material. In some embodiments, the first region 357 and the second region 358 of the cover 352 can have different characteristics, for example but not limited to, different radial strengths, different surface textures, different surface topographies, and/or different coatings.

In an embodiment of the disclosure, the first region 357 of the cover 352 may include a variably permeable microstructure. At least one hydrophilic coating comprising at least one therapeutic agent may be disposed on the expandable member 354. During use, with the first region 357 positioned around the expandable member 354, the underlying hydrophilic coating becomes hydrated or partially hydrated and facilitates fluid transfer across the first region 357 of the cover 352. However, the closed microstructure of the first region 357 in the unexpanded state prevents unwanted, premature release of the therapeutic agent in the unexpanded state. Upon expansion, the orientation or configuration of the microstructure of the material comprising the first region 357, which is disposed over the expandable member, transforms from a substantially closed microstructure to a substantially open microstructure allowing the hydrated or partially hydrated coating to be transferred outward. This feature of the microstructure of the material is one embodiment of a material having a variably permeable microstructure. Once the hydrated or partially hydrated hydrophilic coating passes through the first region 357 of the cover 352, the therapeutic agent is delivered to the treatment site. In one embodiment, the hydrated or partially hydrated coating comprises a therapeutic agent and once the first region 357 is expanded, the therapeutic agent transfers through the first region 357 of the cover 352. In another embodiment, the first region 357 of the cover 352 has a relatively closed microstructure when there is no strain on the outer sheath. In another embodiment, the first region 357 has a more open microstructure when the first region 357 is strained (i.e., diametrically strained). The strain on the first region 357 can be exerted by the underlying expandable member during expansion.

Materials which may exhibit variably permeable microstructures are known to the art. These include, but are not limited to, fibrillated structures, such as expanded fluoropolymers (for example, ePTFE) or expanded polyethylene (as described in U.S. Pat. No. 6,743,388); fibrous structures (such as woven or braided fabrics; non-woven mats of fibers, microfibers, or nanofibers; materials made from processes such as electrospinning or flash spinning; polymer materials consisting of melt or solution processable materials such as fluoropolymers, polyamides, polyurethanes, polyolefins, polyesters, polyglycolic acid (PGA), polylactic acid (PLA), and trimethylene carbonate (TMC), and the like; films with openings created during processing (such as laser- or mechanically-drilled holes); open cell foams; microporous membranes made from materials such as fluoropolymers, polyamides, polyurethanes, polyolefins, polyesters, PGA, PLA, TMC, and the like; porous polyglycolide-co-trimethylene carbonate (PGA:TMC) materials (as described in U.S. Pat. No. 8,048,503); or combinations of the above. Processing of the above materials may be used to modulate, enhance or control permeability between a first, closed state and second, expanded. Such processing may help close the microstructure (thus lower permeability) in a first state, help open the microstructure in a second state, or a combination of both. Such processing which may help close the microstructure may include, but is not limited to: calendaring, coating (discontinuously or continuously), compaction, densification, coalescing, thermal cycling, or retraction and the like. Such processing that may help open the microstructure may include, but is not limited to: expansion, perforation, slitting, patterned densification and/or coating, and the like. In another embodiment, the materials comprise micropores between nodes interconnected by fibrils, such as in ePTFE. In another embodiment, the material comprises micropores in an essentially nodeless ePTFE, as described in U.S. Pat. No. 5,476,589.

Once the therapeutic agent has been eluted through the first region 357 by the expansion of the first region 357 of the cover 352, the expandable member may be deflated and the cover 352 may be pulled through a cover lumen of the catheter 353 to move the second region 358 to be positioned about the expandable member 354. The second region 358 may have a different permeable microstructure than the first region 357. In some embodiments, the second region 356 may have a different nominal diameter than the first region 357, a different surface topography, a different inflation profile, a different inflation sequence, and/or an additional coating on a surface of the second region 356, as compared to the first region 357.

Figure 12:
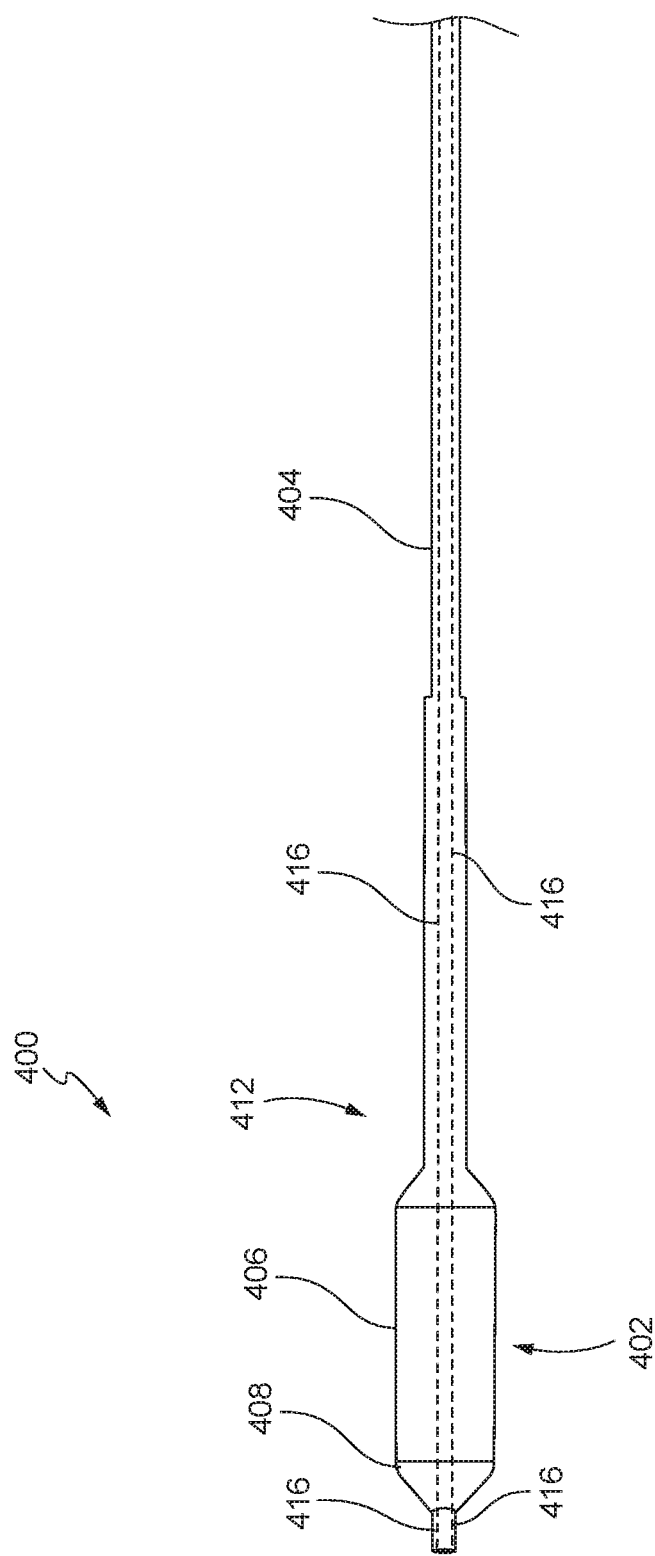
FIG. 12 is a side view of an expandable member assembly including a cover disposed along an expandable member, in accordance with an embodiment of the disclosure.

FIG. 12 depicts a medical device 400 comprising an expandable member assembly 402 and a catheter 404 according to an embodiment of the disclosure. The expandable member assembly 402 may include a cover 406 positioned around an expandable member 408 at a distal section 410 of the catheter 404. The cover 406 may extend along a length of the catheter 404 beyond a proximal end 412 of the expandable member 408. In some embodiments, the cover 406 may not fully surround the expandable member 408, as shown at the distal end 414. The cover 406 may not fully surround the catheter 404. Expandable member assembly 402, in the embodiment depicted in FIG. 12, may comprise one or more lines 416. The lines 416 may be inverted in a lumen of the catheter 404 and may be attached to an actuator (not shown) that can pull the cover 406 into and through a cover lumen of the catheter 404. In some embodiments, the one or more lines 416 are integral with the cover 406. In some embodiments, the one or more lines 416 are coupled to the cover 406.

Figure 13:
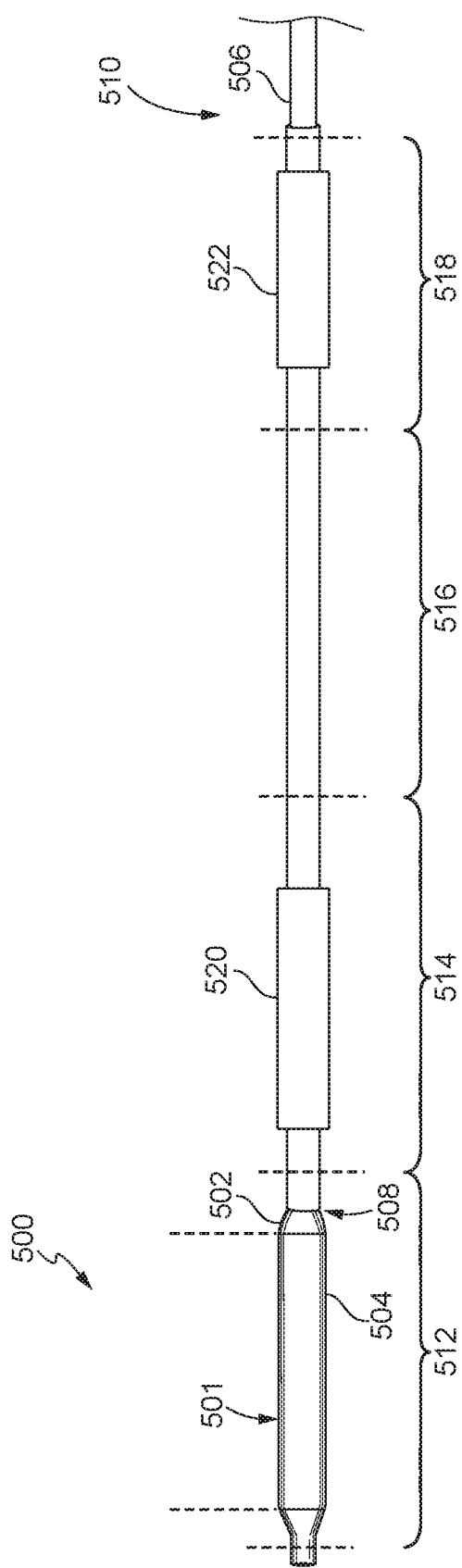
FIG. 13 is a side view of an expandable member assembly including a cover disposed along an expandable member, in accordance with an embodiment of the disclosure.

FIG. 13 depicts a medical device 500 including an expandable member assembly 501 according to an embodiment of the disclosure. The expandable member assembly 501 includes a cover 502 overlaying an expandable member 504. The medical device 200 can include a catheter 506 to which the expandable member 504 and the cover 502 are attached. The catheter 506 may be in fluid communication with the expandable member 504, such that fluid can be introduced through catheter 506 into expandable member 504. The cover 502 is disposed on an outer surface of the expandable member 504 and extends beyond a proximal end 508 of the expandable member 504 along a length of the catheter 506 towards a proximal end 510 of the catheter 506. The cover 502 may have a length that is two, three, four or more times greater than a working length of the expandable member 502 at a nominal diameter. Though not shown in FIG. 13, in some embodiments a sheath may be disposed about at least a portion of the cover 502 that extends along the catheter 506.

The cover 502 may include multiple regions, for example but not limited to a first region 512, a second region 514, a third region 516, and a fourth region 518. In some embodiments, the cover 502 may include more or fewer regions. The various regions 512, 514, 516, and 518 may have the same or different characteristics including nominal diameters, surface topographies, endoprosthesis, and/or therapeutic coatings. In the embodiment of the present disclosure shown in FIG. 13, the first region 512 of the cover 502 may include a characteristic that acts as a pre-treatment to a wall of a vessel prior to delivering an endoprosthesis (e.g., a stent) via a different region of the cover 502. In some embodiments, the characteristic that acts as a pre-treatment may include a therapeutic coating (e.g., paclitaxel), a surface topography (e.g., a surface topography for removing plaque and/or other deposits from the wall of the vessel), or other suitable pre-treatment characteristics. In certain embodiments, the pre-treatment may be applying a vibration of the expandable member 504, and in such embodiments the first region 512 may be strips or lines of the cover 502 and may not surround the expandable member 504 entirely. In some embodiments, the surface topography of the first region 512 may include apertures through which the expandable member 504 may expand and contact the wall of the vessel.

After expanding the expandable member 504 with the first region 512 of the cover 502 positioned about the expandable member 504 to provide the pre-treatment of the first region 512, the expandable member 504 may be deflated and the cover 502 may be pulled through a cover lumen in the catheter 506 and moved through the cover lumen towards the proximal end 510 of the catheter 506. As the first region 514 of the cover 502 is pulled off the expandable member 504 and through the cover lumen, the second region 514 of the cover 502 is moved in position around the expandable member 504.

The expandable member 504 may be reinflated with the second region 514 positioned about the expandable member 504. The second region 514 of the cover 502 may include an endoprosthesis, for example but not limited to a stent 520. The stent 520 may be positioned about the second region 514 of the cover 502 and may be positioned about the expandable member 504 when the second region 514 is positioned about the expandable member 504. The stent 520 may be a self-expanding stent, an expandable stent that is expanded by the expansion of the expandable member, or any other suitable types of stent, though in some embodiments other types of endoprosthesis may be used. With the second region 514 of the cover 502 positioned about the expandable member 504, the stent 520 may be deployed within the wall of the vessel. In some embodiments, the second region 514 of the cover 502 may also have a specific sequence of inflation (e.g., inflating from the middle region outwards to the end of the expandable member), a specific inflation shape (e.g., a consistent diameter along a working length of the expandable member), or other characteristics related to the inflation profile of the expandable member assembly that may correspond to the type of endoprosthesis being deployed (e.g., may inflate from the center outwards, or from the ends inwards). Upon deployment of the stent 520 the expandable member 504 may be deflated and the second region 514 may be pulled through the cover lumen of the catheter 506 to position the third region 516 of the cover 502 about the expandable member 504.

The expandable member 504 may be reinflated with the third region 516 positioned about the expandable member 504. The third region 516 of the cover 502 may include a characteristic that acts as a post-treatment to the wall of the vessel subsequent to delivering the endoprosthesis (e.g., stent 520). The characteristic that acts as a post-treatment may include a therapeutic coating, for example but not limited to a therapeutic coating that minimizes stent restenosis, provides an anti-inflammatory effect, statins, atherosclerosis reversal, or other suitable post-treatment characteristics. Upon reinflation of the expandable member 504 with the third region 516 positioned about the expandable member 504, the third region 516 may contact and provide the post-treatment to the wall of the vessel. In some embodiments, the cover 502 may not include a region for providing a post-treatment. In still yet other embodiments, the cover 502 may include multiple regions for providing one or more post-treatments after delivery of an endoprosthesis. After the inflation and expansion of the expandable member 504 with the third region 516 positioned about the expandable member 504 for providing the post-treatment, the expandable member 504 may be deflated and the cover 502 may be pulled through the cover lumen of the catheter 506 to position the third region 516 of the cover 502 about the expandable member 504.

The expandable member 504 may be reinflated with the fourth region 518 positioned about the expandable member 504. The fourth region 518 of the cover 502 may include another endoprosthesis, for example but not limited to an additional stent 522. The additional stent 522 may be the same type of stent as stent 520 or may be a different type of stent 520. In some embodiments, the stent 522 may be the same type of stent as stent 520 but may have a different diameter and/or a different length. With the fourth region 518 of the cover 502, including the additional stent 522, positioned about the expandable member 504, the expandable member 504 may be inflated and the stent 522 may be deployed within the wall of the vessel. In some embodiments, the fourth region 518 of the cover 502 may also have a specific sequence of inflation (e.g., inflating from the middle region outwards to the end of the expandable member), a specific inflation shape (e.g., a consistent diameter along a working length of the expandable member), or other characteristics related to the inflation profile of the expandable member assembly that may correspond to the type of endoprosthesis being deployed (e.g., may inflate from the center outwards, or from the ends inwards). Upon deployment of the additional stent 522 the expandable member 504 may be deflated and the medical device 500 may be removed from the vessel of the patient. As described above with reference to FIG. 13, the medical device 500 that includes the cover 504 may permit the application of multiple treatments to the wall of a vessel without the removal of the medical device 500, for example but not limited to providing for a pre-treatment, deployment of a stent, post-treatment, and the deployment of an additional stent. In some embodiments, the cover 504 may include more or fewer regions and each of the characteristics of the various regions of the cover 504 may be altered, removed, or otherwise changed. In some embodiments, additional endoprosthesis may be deployed, different pre and/or post treatments may be applied, additional or fewer pre or post treatments may be applied, and/or other changes to the characteristics of the regions of the cover 504 may be made.

As described herein, a cover of an expandable member assembly can comprise a plurality of regions having the same or different characteristics. The chart below provides examples of various combinations of the features described above with respect to one or more embodiments of the present disclosure. The chart below is not an exhaustive list of potential combinations as additional combinations of features are contemplated by this disclosure. In addition, "Region 1," "Region 2," Region 3," and "Region 4" as recited below do not indicate any order of placement of the regions along a length of the catheter. For example, Region 3 may be positioned adjacent Region 1 and Region 4 etc. Nor does "Region 1," "Region 2," Region 3," and "Region 4" indicate an order of deployment during use. In addition, the identification of a drug as "Drug 1," "Drug 2," "Drug 3," "Drug 4" or when used in the same Example denotes a different drug. Thus, each of Drug 1, Drug 2, Drug 3, and Drug 4 in a single Example is optionally selected from the non-exclusive list of drugs below the heading "Therapeutic Agents" provided above, so long as each of Drug 1, Drug 2, Drug 3, and Drug 4 are different in each Example in which they appear together. Thus, "Drug 1" or similar notation (e.g. "Shape 1," "Texture 1," "Endoprosthesis 1") repeated in a single Example refers to the same Drug (or other characteristic) within a single Example, but each such term does not indicate the same drug (shape or texture) between Examples. For example, "Drug 1" in Example No. 1 may be a different drug than "Drug 1" in Example No. 2, similarly "Shape 1" in Example No. 2 may be different than "Shape 1" in Example No. 3. Moreover, this list is not exhaustive any characteristic listed may be replaced by another, different characteristic.

Texture, as used below refers to a surface topography, for example but not limited to the surface topographies disclosed specifically herein (e.g., a surface topography defined by apertures, scored portions, beads, filaments, fibers, rings, knits, weaves, braids, and/or a densified material that alters a coefficient of friction of a surface of the cover). Shape, as used below refers to an inflation profile (e.g., a particular nominal diameter, working length, or other inflation shape) or a sequence of inflation along the region of the cover. Endoprosthesis, as used below refers to the inclusion of an endoprosthesis on the region of the cover (e.g., a stent). In some of the Examples below an "x" is used to indicate the cover does not include the region. In addition, each Example below could be modified by removing a region, adding a region, or changing a feature or characteristic of a region.

| Example | Region 1 | Region 2 | Region 3 | Region 4 |
| --- | --- | --- | --- | --- |
| Example No. 1 | No Drug | Drug 1 | Drug 2 | Drug 3 |
| Example No. 2 | No Drug | Drug 1 | Drug 2 | Shape 1 |
| Example No. 3 | No Drug | Drug 1 | Shape 1 | Shape 2 |
| Example No. 4 | No Drug | Texture 1 | Drug 1 | Shape 1 |
| Example No. 5 | No Drug | Texture 1 | Drug 1 | Drug 2 |
| Example No. 6 | No Drug | Texture 1 | Shape 1 | Shape 2 |
| Example No. 7 | No Drug | Texture 1 | Texture 2 | Shape |
| Example No. 8 | Shape 1 | No Drug | Drug 1 | Drug 2 |
| Example No. 9 | Shape 1 | Drug 1 | Drug 2 | Drug 3 |
| Example No. 10 | Shape 1 | Drug 1 | Drug 2 | Texture 1 |
| Example No. 11 | Shape 1 | Drug 1 | Texture 1 | Texture 2 |
| Example No. 13 | Shape 1 | Drug 1 | Drug 2 | Shape 2 |
| Example No. 14 | Drug 1 | Drug 1 | Drug 2 | Drug 2 |
| Example No. 15 | Drug 1 | Drug 1 | Drug 1 | Drug 1 |
| Example No. 16 | Drug 1 | Drug 2 | Drug 3 | Drug 4 |
| Example No. 17 | Drug 1 | Drug 2 | Drug 3 | Drug 3 |
| Example No. 18 | Texture 1 | Texture 2 | Drug 1 | Drug 2 |
| Example No. 19 | Texture 1 | Texture 2 | Texture 3 | Shape 1 |
| Example No. 20 | Texture 1 | Texture 2 | Shape 1 | Shape 2 |
| Example No. 21 | Texture 1 | Shape 1 | Shape 2 | Drug 1 |
| Example No. 22 | Texture 1 | Drug 1 | Drug 2 | Drug 3 |
| Example No. 23 | Texture 1 | Drug 1 | Drug 2 | Shape 1 |
| Example No. 24 | Texture 1 | Shape 1 | Drug 1 | Drug 1 |
| Example No. 25 | Texture 1 | Drug 1 | Shape 1 | x |
| Example No. 26 | Texture 1 | Drug 1 | Drug 2 | x |
| Example No. 27 | Drug 1 | Drug 2 | Drug 3 | x |
| Example No. 28 | Texture 1 | Drug 1 | Drug 2 | x |
| Example No. 29 | Drug 1 | Drug 1 | Shape 1 | x |
| Example No. 30 | Drug 1 | Drug 2 | Shape 1 | x |
| Example No. 32 | Shape 1 | Shape 2 | Shape 3 | x |
| Example No. 33 | Texture 1 | Texture 2 | Drug 1 | x |
| Example No. 34 | Drug 1 | Drug 2 | x | x |
| Example No. 35 | Drug 1 | Drug 1 | x | x |
| Example No. 36 | Texture 1 | Drug 1 | x | x |
| Example No. 37 | Drug 1 | Surface 1 | x | x |
| Example No. 38 | Texture 1 | Surface 1 | x | x |
| Example No. 39 | Surface 1 | Surface 2 | x | x |
| Example No. 40 | Texture 1 | Texture 2 | x | x |
| Example No. 41 | No Drug | Drug 1 | Texture 1 | Endoprosthesis 1 |
| Example No. 42 | Drug 1 | Texture 1 | Endoprosthesis 1 | Drug 2 |
| Example No. 43 | Drug 1 | Texture 1 | Texture 2 | Endoprosthesis 1 |
| Example No. 44 | Drug 1 | Texture 1 | Endoprosthesis 1 | Endoprosthesis 2 |
| Example No. 45 | Drug 1 | Endoprosthesis 1 | Endoprosthesis 2 | Drug 2 |
| Example No. 46 | Endoprosthesis 1 | Endoprosthesis 2 | Endoprosthesis 3 | Endoprosthesis 4 |
| Example No. 47 | Texture 1 | Texture 2 | Texture 3 | Endoprosthesis 1 |
| Example No. 48 | Drug 1 | Drug 1 | Texture 1 | Endoprosthesis 1 |
| Example No. 49 | Shape 1 | Drug 1 | Texture 1 | Endoprosthesis 1 |
| Example No. 50 | Shape 1 | Endoprosthesis 1 | Drug 1 | Drug 2 |

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method of treatment comprising:
providing a medical device having an expandable member and a cover, the cover further comprising a first region and a second region;
inserting the medical device in a peripheral blood vessel;
expanding the expandable member with the first region of the cover positioned over the expandable member such that the first region of the cover provides a first treatment to a blood vessel wall;
activating an actuator to draw the first region into a lumen of the medical device and to position the second region of the cover over the expandable member; and
expanding the expandable member with the second region of the cover over the expandable member such that the second region of the cover provides a second treatment to the blood vessel wall,
wherein the first treatment is different from the second treatment, and each of the first treatment and the second treatment is provided to the blood vessel wall prior to removing the medical device assembly from the body lumen.

2. The method of treatment of claim 1, wherein at least one of the first treatment and the second treatment comprises transferring a therapeutic agent to the blood vessel wall.

3. The method of treatment of claim 2, wherein the second region of the cover includes a plurality of apertures through which an expandable member expands and wherein providing the second treatment comprises contacting and shaving deposits from a surface of blood vessel wall.

4. The method of treatment of claim 3, further comprising expanding the expandable member with a third region of the cover over the expandable member such that the third region of the cover provides a third treatment to the blood vessel wall, wherein each of the first treatment, the second treatment, and the third treatment is provided to the blood vessel wall prior to removing the medical device assembly from the blood vessel.

5. The method of treatment of claim 4, wherein the third treatment comprises positioning an endoprosthesis positioned around the third region of the cover into contact with at least a portion of the blood vessel wall.

6. The method of treatment of claim 2, wherein the first treatment comprises transferring a first therapeutic agent to the blood vessel wall, and wherein the second treatment comprises transferring a second therapeutic agent to the blood vessel wall, the first therapeutic agent being different from the second therapeutic agent.

7. The method of treatment of claim 2, further comprising expanding the expandable member with a third region of the cover over the expandable member such that the third region of the cover provides a third treatment to the blood vessel wall, wherein the third region of the cover comprises an endoprosthesis and the third treatment comprises deploying the endoprosthesis in the blood vessel wall, and wherein each of the first treatment, the second treatment, and the third treatment is provided to the blood vessel wall prior to removing the medical device assembly from the body lumen.

8. The method of treatment of claim 7, wherein the first treatment is performed prior to the third treatment, and wherein the first treatment comprises contacting and shaving deposits from a surface of blood vessel wall.

9. The method of treatment of claim 7, wherein the first treatment comprises transferring a first therapeutic agent to the blood vessel wall.

10. The method of treatment of claim 7, wherein the first treatment is performed prior to the third treatment, and wherein the second treatment is performed after the third treatment.

11. The method of treatment of claim 10, wherein the second treatment comprises transferring a therapeutic agent to the blood vessel wall.

12. The method of treatment of claim 10, wherein the second region comprises an endoprosthesis and wherein the second treatment comprises deploying a second endoprosthesis in the blood vessel well.

13. The method of treatment of claim 12, wherein a first diameter the endoprosthesis of the third region is different from a second diameter of the second endoprosthesis of the second region.

14. The method of treatment of claim 12, wherein a first length of the endoprosthesis of the third region is a different from a second length of the second endoprosthesis of the second region.

15. The method of treatment of claim 12, further comprising expanding the expandable member with a fourth region of the cover over the expandable member such that the fourth region of the cover provides a fourth treatment to the blood vessel wall.

16. The method of treatment of claim 15, wherein each of the first treatment, the second treatment, the third treatment, and the fourth treatment is provided to the blood vessel wall prior to removing the medical device assembly from the body lumen.

* * * * *